United States Patent
Kobayashi et al.

(10) Patent No.: US 10,045,818 B2
(45) Date of Patent: Aug. 14, 2018

(54) TREATMENT TOOL FOR ENDOSCOPE AND INCISION SYSTEM

(71) Applicant: OLYMPUS CORPORATION, Hachioji-shi, Tokyo (JP)

(72) Inventors: Tsukasa Kobayashi, Tokyo (JP); Yuji Sakamoto, Tokyo (JP); Hiroyuki Morishita, Tokyo (JP); Isamu Nakajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/225,486

(22) Filed: Aug. 1, 2016

(65) Prior Publication Data
US 2016/0338771 A1  Nov. 24, 2016

Related U.S. Application Data

(63) Continuation of application No. PCT/JP2015/056078, filed on Mar. 2, 2015.

(30) Foreign Application Priority Data

Mar. 4, 2014  (JP) .................. 2014-042050

(51) Int. Cl.
*A61B 18/14* (2006.01)
*A61B 18/00* (2006.01)

(52) U.S. Cl.
CPC .............. *A61B 18/1492* (2013.01); *A61B 2018/00494* (2013.01); *A61B 2018/00982* (2013.01); *A61B 2018/144* (2013.01)

(58) Field of Classification Search
CPC .............. A61B 18/149; A61B 18/1492; A61B 2018/00494; A61B 2018/144;
(Continued)

(56) References Cited

U.S. PATENT DOCUMENTS

| 5,163,938 A * | 11/1992 | Kambara | A61B 18/14 606/47 |
| 6,471,702 B1 * | 10/2002 | Goto | A61B 18/14 606/46 |

(Continued)

FOREIGN PATENT DOCUMENTS

| JP | S61-67710 U | 5/1986 |
| JP | H04-364836 A | 12/1992 |

(Continued)

OTHER PUBLICATIONS

May 19, 2015 Search Report issued in International Patent Application No. PCT/JP2015/056078.

*Primary Examiner* — Thomas Giuliani
(74) *Attorney, Agent, or Firm* — Oliff PLC

(57) ABSTRACT

A treatment tool for an endoscope includes a sheath which is extended along a longitudinal axis; a pre-curved portion which is disposed at a distal portion of the sheath; a knife wire lumen which is formed along the longitudinal axis of the sheath; a first communication hole and a second communication hole which are open on an outer circumferential surface to communicate the outer circumferential surface positioned with the knife wire lumen; a wire-shaped cutting portion which is protruded from the first communication hole and the second communication hole, and is extended in a position spaced from the outer circumferential surface and the virtual plane; a fixing portion which is provided to fix an end portion of a wire connected to the cutting portion inside the knife wire lumen, and a bending portion which is provided to bend the wire.

4 Claims, 20 Drawing Sheets

(58) Field of Classification Search
CPC .... A61B 2018/00982; A61B 2018/141; A61B 2018/00553; A61B 2018/1407; A61B 2018/00601
USPC .................................. 606/37, 39, 41, 45–47
See application file for complete search history.

(56) References Cited

U.S. PATENT DOCUMENTS

| | | |
|---|---|---|
| 6,606,515 B1 | 8/2003 | Windheuser et al. |
| 2002/0120253 A1 | 8/2002 | Ouchi |
| 2005/0049454 A1* | 3/2005 | Ouchi ................ A61B 18/1492 600/105 |
| 2009/0048487 A1* | 2/2009 | Yanuma ............. A61B 18/1492 600/139 |

FOREIGN PATENT DOCUMENTS

| | | |
|---|---|---|
| JP | H09-56666 A | 3/1997 |
| JP | 2000-237202 A | 9/2000 |
| JP | 2001-070316 A | 3/2001 |
| JP | 2001-511023 A | 8/2001 |
| JP | 2002-035003 A | 2/2002 |
| JP | 2003-024346 A | 1/2003 |
| JP | 2009-045451 A | 3/2009 |
| WO | 98/10821 A1 | 3/1998 |

* cited by examiner

TREATMENT TOOL FOR ENDOSCOPE AND INCISION SYSTEM

This application is a continuation application based on a PCT International Application No. PCT/JP2015/056078, filed on Mar. 2, 2015, whose priority is claimed on Japanese Patent Application No. 2014-042050, filed on Mar. 4, 2014. The contents of both the PCT International Application and the Japanese Patent Application are incorporated herein by reference.

BACKGROUND OF THE INVENTION

Field of the Invention

The present invention relates to a treatment tool for an endoscope and an incision system.

Description of Related Art

As a procedure for incising the sphincter of a duodenal papilla portion while observing a duodenal papilla using an endoscope apparatus, endoscopic sphincterotomy (EST) is known. For example, a treatment tool which is used in the EST is disclosed in U.S. Pat. No. 6,606,515, Japanese Unexamined Patent Application, First Publication No. 2001-070316, Japanese Unexamined Patent Application, First Publication No. 2000-237202, and Published Japanese Translation No. 2001-511023 of the PCT International Publication. U.S. Pat. No. 6,606,515 discloses a guide wire insertion tool in which a funnel-shaped extension portion is provided, which communicates with a lumen of a catheter in order to easily insert a guide wire into the lumen of the catheter. Japanese Unexamined Patent Application, First Publication No. 2001-070316 discloses a high-frequency knife in which a guide arm portion is formed on a knife wire, and a cutting portion of the knife wire can be directed to a desired direction by disposing the guide arm portion in a slit which is formed in a sheath. Japanese Unexamined Patent Application, First Publication No. 2000-237202 discloses a treatment tool which can safely perform the EST by providing a cutting portion which is not insulated, and an insulation portion which is insulated in a portion except for the cutting portion, on a distal end portion of a high frequency knife wire. Published Japanese Translation No. 2001-511023 of the PCT International Publication discloses a bile duct treatment catheter which includes a groove which communicates with a guide wire lumen from a position outside a catheter shaft and extends in a longitudinal direction of the shaft so as to easily replace a guide wire.

SUMMARY OF THE INVENTION

According to a first aspect of the present invention, a treatment tool for an endoscope includes a sheath which is extended along a longitudinal axis; a pre-curved portion which is disposed at a distal portion of the sheath, and has a restoring force to restore the pre-curved portion to a curved shape in which a center axis of the sheath is curved in a predetermined virtual plane; a knife wire lumen which is formed along the longitudinal axis of the sheath; a first communication hole which is open on an outer circumferential surface positioned at an inward side of the curved shape, and communicates the outer circumferential surface positioned at the inward side of the curved shape with the knife wire lumen; a second communication hole which is open on the outer circumferential surface positioned at the inward side of the curved shape, and communicates the outer circumferential surface positioned at an inward side of the curved shape with the knife wire lumen at a more proximal position of the pre-curved portion than the first communication hole; a wire-shaped cutting portion which is protruded from the first communication hole and the second communication hole in a state that the pre-curved portion is curved to the curved shape, and is extended in a position spaced from the outer circumferential surface positioned at the inward side of the curved shape and the virtual plane between the first communication hole and the second communication hole, the cutting portion being capable of incising tissues; a fixing portion which fixes an end portion of a wire connected to the cutting portion inside the knife wire lumen, and a bending portion which bends the wire extending from the end portion of the wire to the cutting portion from a direction in which the first communication hole is open to a direction away from the outer circumferential surface positioned at the inward side of the curved shape and the virtual plane.

According to a second aspect of the present invention, in the treatment tool for an endoscope according to the first aspect, a guide wire lumen through which a guide wire is capable of being inserted may be formed at the pre-curved portion, and the virtual plane may cross an inner wall of the guide wire lumen.

According to a third aspect of the present invention, the treatment tool for an endoscope according to the first aspect may further include a liquid feed and discharge lumen which is formed along the center axis of the sheath such that the virtual plane is positioned at a wall portion between the liquid feed and discharge lumen and the knife wire lumen and includes a space which is capable of being used for feeding and discharging liquid.

According to a fourth aspect of the present invention, in the treatment tool for an endoscope according to the second aspect, the guide wire lumen may be formed at a position at which the center axis of the sheath and the center axis of the guide wire lumen are included in the virtual plane.

According to a fifth aspect of the present invention, in the treatment tool for an endoscope according to the first aspect, the pre-curved portion may include a first curved portion which has a restoring force so as to be restored to the curved shape in which the center axis of the sheath is included in the virtual plane; and a second curved portion which is continuous to a proximal end of the first curved portion and has a restoring force so as to be restored to the curved shape in the same direction as that of the first curved portion, the second curved portion being provided to guide the distal portion of the pre-curved portion, wherein the second curved portion is rotated around the center axis of the sheath with respect to the treatment tool channel, and the distal portion of the pre-curved portion is in a predetermined direction when the second curved portion is protruded from an opening portion of the treatment tool channel, by inserting the second curved portion through a treatment tool channel which is bent by a bendable portion of an endoscope.

According to a sixth aspect of the present invention, in the treatment tool for an endoscope according to the first aspect, the knife wire lumen may include a center axis at a position away from the virtual at a distal end portion of the pre-curved portion, the first communication hole may be formed at a position at the inward side of the curved shape and away from the virtual plane, and the second communication hole may be formed at a position at the inward side of the curved shape and away from the virtual plane.

According to a seventh aspect of the present invention, in the treatment tool for an endoscope according to the first aspect, the treatment tool for an endoscope may be used together with an endoscope including a bendable portion that actively deforms a treatment tool channel to be bent, the curved shape of the pre-curved portion may be curved so as to rotate around the longitudinal axis of the sheath in a state that the curved shape is passed through the treatment tool channel that is bent by the bendable portion of the endoscope, and the cutting portion may be curved by the bending portion such that the cutting portion is provided to be extended in a position away from the virtual plane including a center axis of the curved shape of the pre-curved portion which is protruded from the treatment tool channel in a state that the pre-curved portion is rotated around the longitudinal axis of the sheath.

According to an eighth aspect of the present invention, the treatment tool for an endoscope according to the first aspect may further include a guide wire accommodation portion which is parallelly formed with the knife wire lumen in the sheath, wherein a slit may be formed at a position at which the outer interferential surface of the pre-curved portion intersects to the virtual plane along the longitudinal axis to communicate with the guide wire accommodation.

According to a ninth aspect of the present invention, an incision system includes a sheath which has a center axis along a longitudinal axis; a pre-curved portion which is disposed at a distal portion of the sheath, and has a restoring force to restore the pre-curved portion to a curved shape in which the center axis of the sheath is curved in a predetermined virtual plane; a knife wire lumen which longitudinal axis of the sheath; a first communication hole which is open in a direction inclined to the virtual plane and in a direction inward of the curved shape, and communicates an outer circumferential surface positioned at an inward side of the curved shape of the pre-curved portion with the knife wire lumen; a second communication hole which is open in a direction inclined to the virtual plane and in a direction inward of the curved shape, and communicates the outer circumferential surface positioned at the inward side of the curved shape of the pre-curved portion with the knife wire lumen at a more proximal position of the pre-curved portion than the first communication hole; a wire-shaped cutting portion which is protruded from the first communication hole and the second communication hole in a state that the pre-curved portion is curved to the curved shape and has a bending portion which is bent across the first communication hole and the second communication hole and passes a position where is away from the outer circumferential surface at the inward side of the curved shape and the virtual plane, the cutting portion being capable of incising tissues; and a fixing portion which is provided to fix an end portion of a wire connected to the cutting portion in the knife wire lumen.

According to a tenth aspect of the present invention, in the incision system according to the ninth aspect, the bending portion of the cutting portion may be intersected to the virtual plane and bent on a second virtual plane, the second virtual plane being approximately parallel with a tangential plane contacting with the outer circumferential surface of the sheath.

According to an eleventh aspect of the present invention, the incision system according to the ninth aspect may further include an operation wire which is continuous to the cutting portion and extends along the longitudinal axis of the sheath; and an operation portion which is provided on a proximal portion of the operation wire and provided to adjust a curvature radius of the pre-curved portion, wherein the bending portion of the cutting portion is deformed from an approximately straight-line shape into a curved shape by operating the operation portion to increase the curvature radius of the pre-curved portion.

According to a twelfth aspect of the present invention, in the incision system according to the ninth aspect, the knife wire lumen may include a center axis at a position away from the virtual plane at a distal end portion of the pre-curved portion, the first communication hole may be formed at a position at the inward side of the curved shape and away from the virtual plane, and the second communication hole may be formed at a position at the inward side of the curved shape and away from the virtual plane.

According to a thirteenth aspect of the present invention, in the incision system according to the ninth aspect, the incision system may be used together with an endoscope including a bendable portion that actively deforms a treatment tool channel to be bent, the curved shape of the pre-curved portion may be curved so as to rotate around the longitudinal axis of the sheath in a state that the curved shape is passed through the treatment tool channel that is bent by the bendable portion of the endoscope, and the cutting portion may be curved by the bending portion such that the cutting portion is provided to be extended in a position away from the virtual plane including a center axis of the curved shape of the pre-curved portion which is protruded from the treatment tool channel in a state that the pre-curved portion is rotated around the longitudinal axis of the sheath.

According to a fourteenth aspect of the present invention, the incision system according to the ninth aspect may further include a guide wire accommodation portion which is parallelly formed to the knife wire lumen in the sheath, wherein a slit may be formed at a position at which the interferential surface of the pre-curved portion intersects to the virtual plane along the longitudinal axis to communicate with the guide wire accommodation.

According to a fifteenth aspect of the present invention, an incision system includes an endoscope which includes an imaging portion which is capable of imaging a target portion, an insertion portion which has a treatment tool channel communicating with an opening portion disposed adjacent to the imaging portion and is inserted into a body, and a bendable portion which is disposed at part of the insertion portion and capable of bending the treatment tool channel; a sheath which has a center axis along a longitudinal axis and is capable of being inserted into the treatment tool channel; a pre-curved portion which is disposed at a distal portion of the sheath, and has a restoring force to restore the pre-curved portion to a curved shape in which the center axis of the sheath is curved in a predetermined virtual plane; a knife wire lumen which is formed along the longitudinal axis of the sheath; a first communication hole which is open in a direction inclined to the virtual plane and in a direction inward of the curved shape, and communicates an outer circumferential surface positioned at an inward side of the curved shape of the pre-curved portion with the knife wire lumen; a second communication hole which is open in a direction inclined to the virtual plane and in a direction inward of the curved shape, and communicates the outer circumferential surface positioned at an inward side of the curved shape of the pre-curved portion with the knife wire lumen at a more proximal position of the pre-curved portion than the first communication hole; a wire-shaped cutting portion which is protruded from the first communication hole and the second communication hole in a state that the pre-curved portion is curved to the curved shape and has a bending portion which is bent across the first communication hole and the second communication hole and passes a position where is away from the outer circumferential surface at the inward side of the curved shape and the virtual plane, the cutting portion being capable of incising tissues; a fixing portion which fixes an end portion of a wire connected to the cutting portion in in the knife wire lumen; and a bending portion which bends the wire extending from the end portion of the wire to the cutting portion from a direction in which the first communication hole is to a direction away from the outer circumferential surface positioned at the inward side of the curved shape and the virtual plane, wherein the outer circumferential surface of the proximal end portion of the pre-curved portion is pressed by a raising stand, in a state that the cutting portion and a distal end portion of the pre-curved portion enter an imaging range of the imaging portion.

According to a sixteenth aspect of the present invention, in the incision system according to the fifteenth aspect, the distal end portion of the pre-curved portion may be a first curved portion which has a restoring force so as to be restored to the curved shape in which the center axis of the sheath is included in the virtual plane, the proximal end portion of the pre-curved portion may be a second curved portion which is continuous to a proximal end of the first curved portion, has a restoring force so as to be restored to the curved shape in the same direction as that of the first curved portion, and determines a position of the cutting portion in the direction around the longitudinal axis of the sheath, the second curved portion may be inserted into the treatment tool channel which is bent by the bendable portion of the endoscope, the second curved portion rotates around the center axis of the sheath with respect to the treatment tool channel, and the distal end portion of the pre-curved portion is directed in a predetermined direction when the second curved portion protrudes from the opening portion of the endoscope, and a bending portion may be bent toward the imaging portion of the endoscope in a state that the distal end portion of the pre-curved portion protrudes from the opening portion of the endoscope.

According to a seventeenth aspect of the present invention, in the incision system according to the fifteenth aspect, the knife wire lumen may include a center axis at a position away from the virtual plane at a distal end portion of the pre-curved portion, the first communication hole may be formed at a position at the inward side of the curved shape and away from the virtual plane, and the second communication hole may be formed at a position at the inward side of the curved shape and away from the virtual plane.

According to an eighteenth aspect of the present invention, in the incision system according to the fifteenth aspect, the curved shape of the pre-curved portion may be curved so as to rotate around the longitudinal axis of the sheath in a state that the curved shape is passed through the treatment tool channel that is bent by the bendable portion of the endoscope, and the cutting portion may be bent by the bending portion such that the cutting portion is provided to be extended in a position away from the virtual plane including a center axis of the curved shape of the pre-curved portion which is protruded from the treatment tool channel in a state that the pre-curved portion is rotated around the longitudinal axis of the sheath.

According to a nineteenth aspect of the present invention, the incision system according to the fifteenth aspect may further include a guide wire accommodation portion which is parallelly formed to the knife wire lumen in the sheath, wherein a slit may be formed at a position at which the interferential surface of the pre-curved portion intersects to the virtual plane along the longitudinal axis to communicate with the guide wire accommodation.

DETAILED DESCRIPTION OF THE INVENTION

Figure 1:
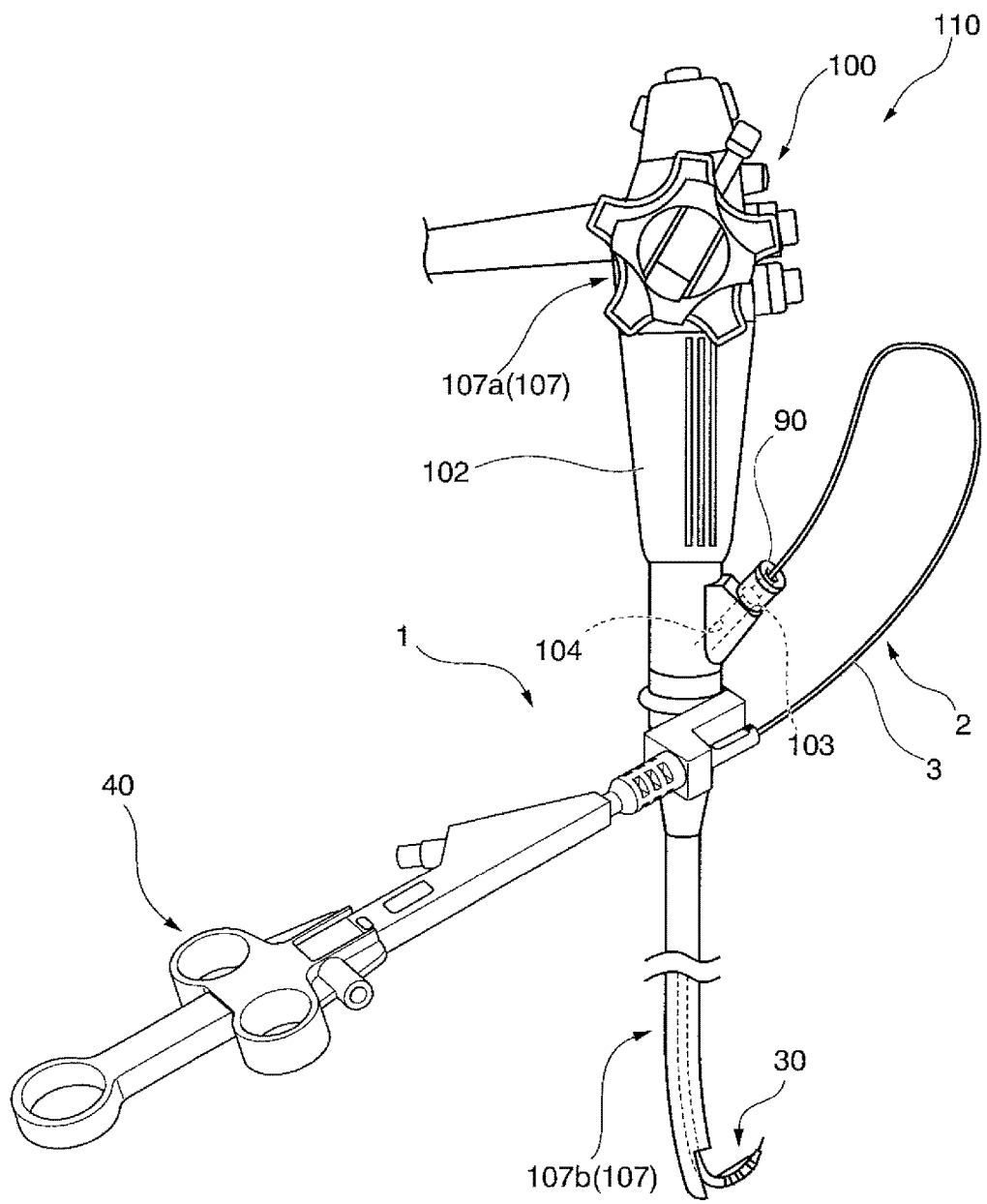
FIG. 1 is an overall view of an incision system including a treatment tool for an endoscope according to a first embodiment of the present invention.

A first embodiment of the present invention will be described. FIG. 1 is an overall view of an incision system 110 which includes a treatment tool 1 for an endoscope according to the present embodiment.

As shown in FIG. 1, the treatment tool 1 for an endoscope according to the present embodiment is a medical instrument which is used along with an endoscope apparatus 100 in order to incise a biological tissue in the body. The treatment tool 1 for an endoscope configures an incision system 110 (endoscope treatment system) in a state of being combined with the endoscope apparatus 100.

Figure 2:
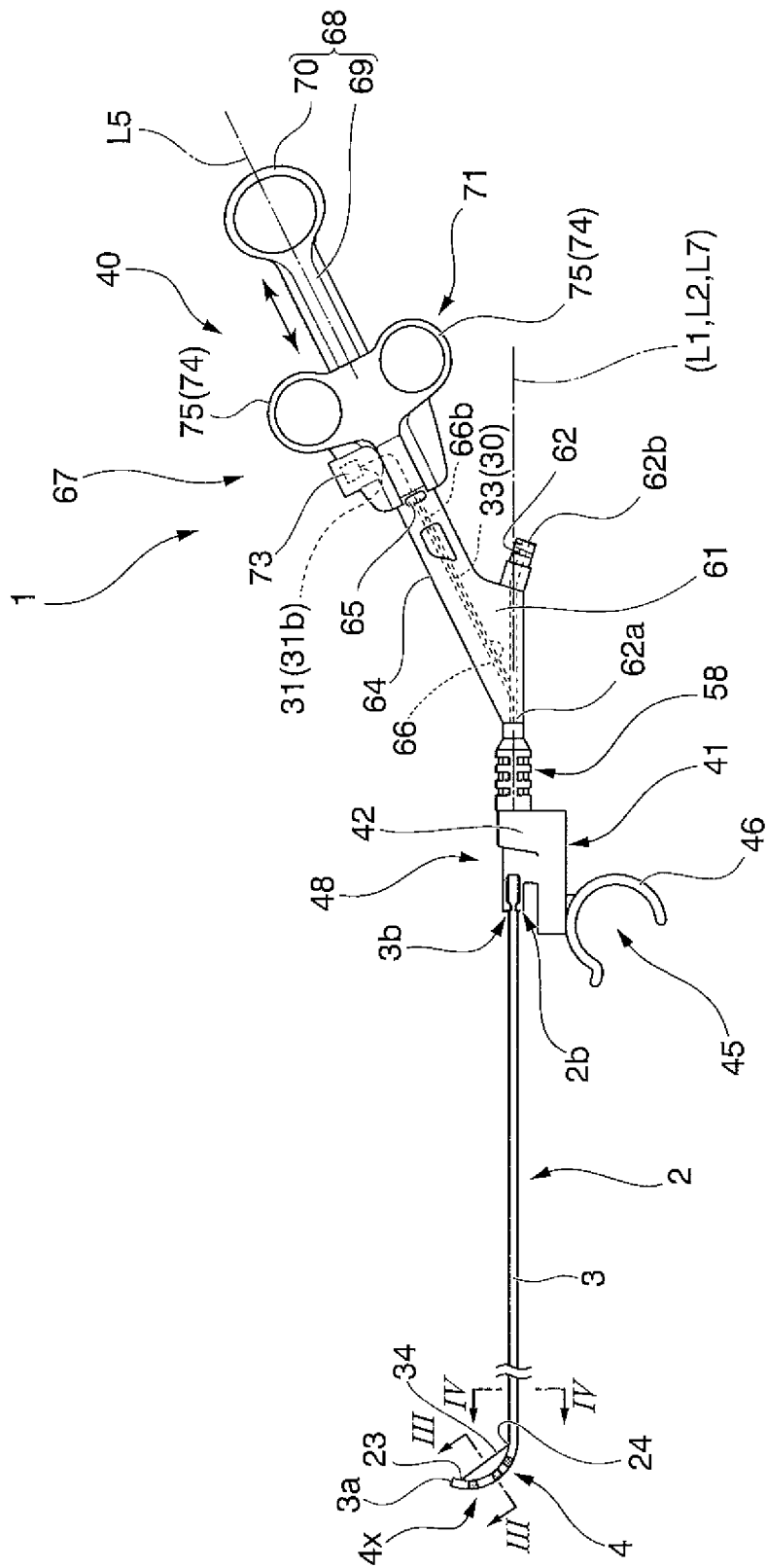
FIG. 2 is a plan view of the treatment tool for an endoscope according to the first embodiment of the present invention.
Figure 3A:
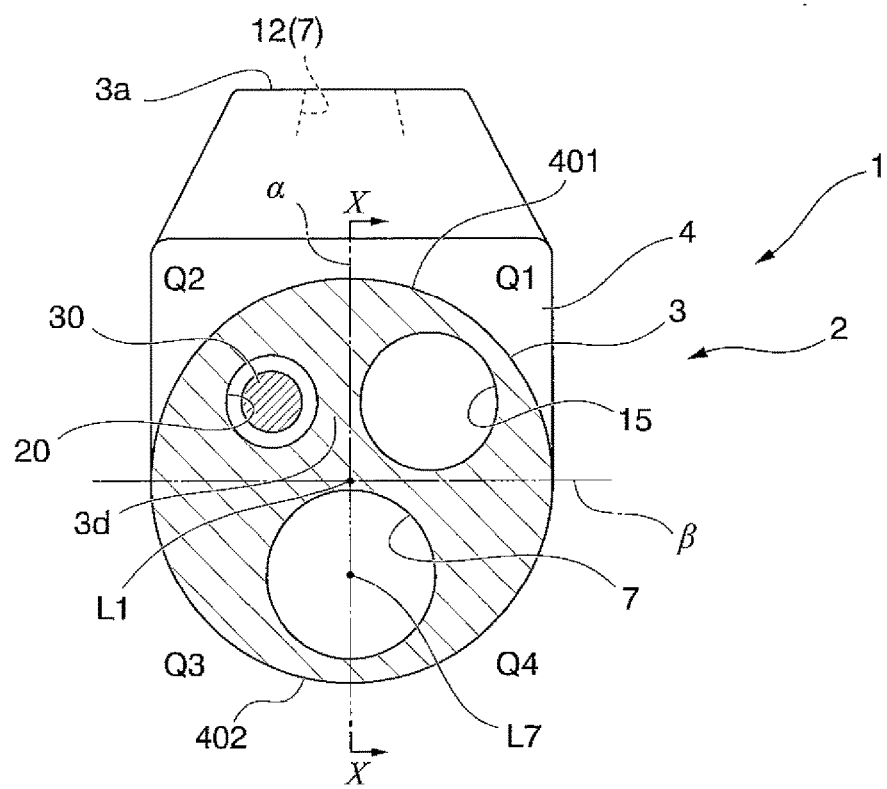
FIG. 3A is a sectional view taken along line III-III of FIG. 2.
Figure 3B:
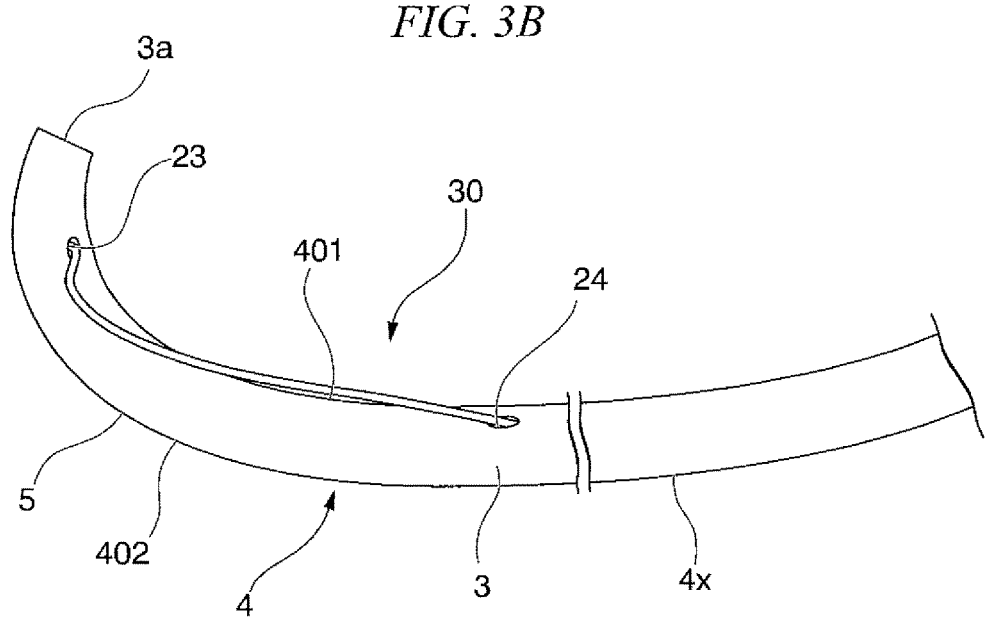
FIG. 3B is a plan view showing a distal end portion of a sheath of the treatment tool for an endoscope according to the first embodiment of the present invention.
Figure 4:
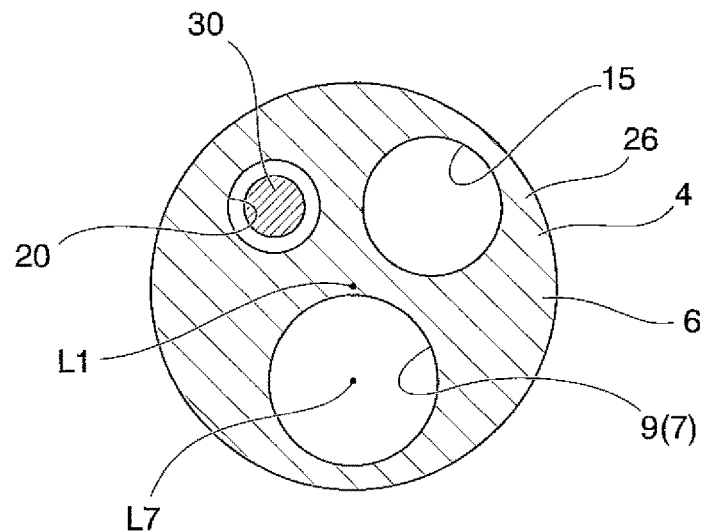
FIG. 4 is a sectional view taken along line IV-IV of FIG. 2.
Figure 5:
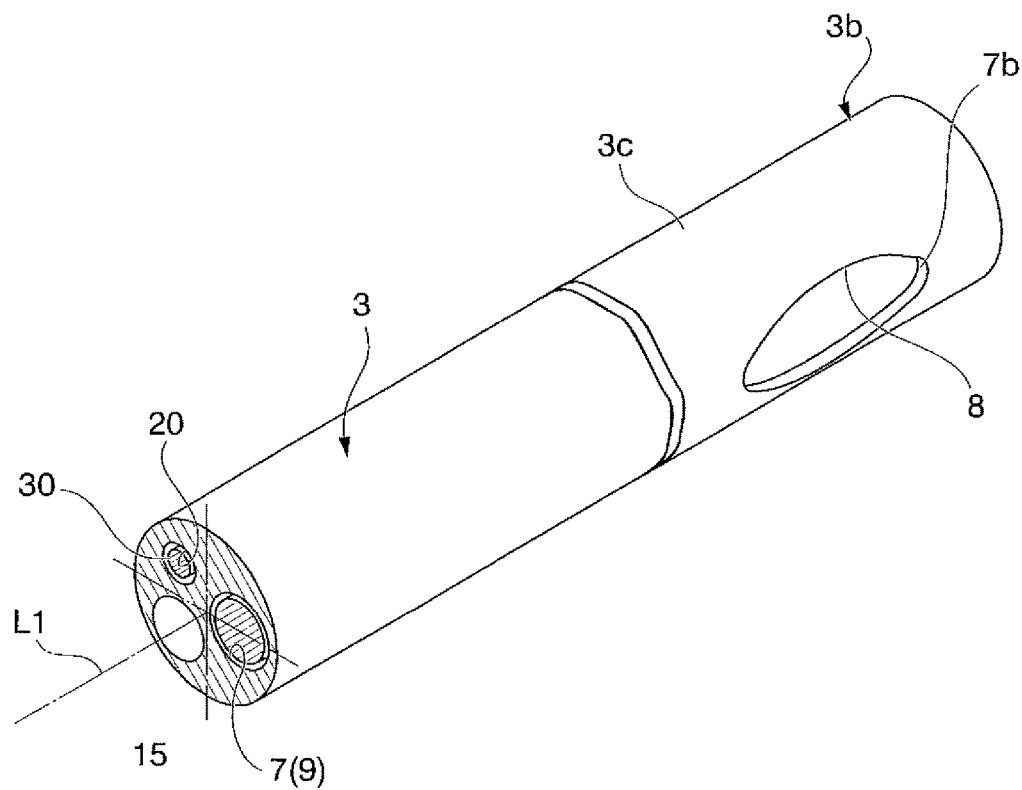
FIG. 5 is a perspective view showing a portion of the sheath in the treatment tool for an endoscope according to the first embodiment of the present invention.
Figure 6:
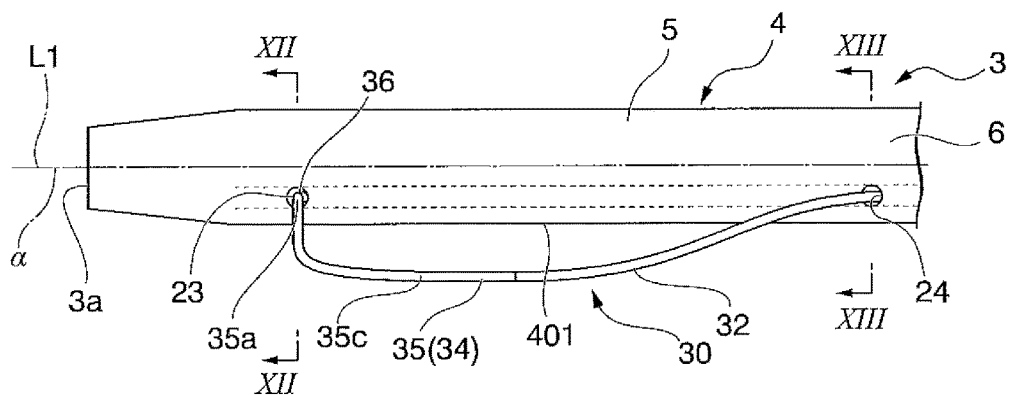
FIG. 6 is a view when the distal portion of the sheath of the treatment tool for an endoscope according to the first embodiment of the present invention is viewed from a direction perpendicular to a second virtual plane.
Figure 7A:
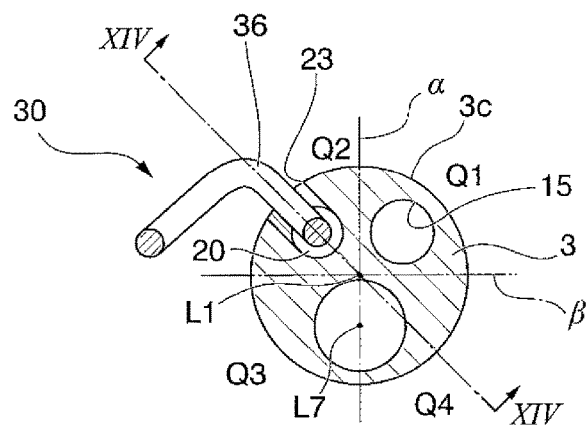
FIG. 7A is a sectional view taken along line XII-XII of FIG. 6.
Figure 8:
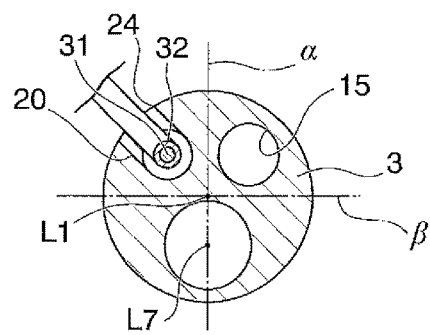
FIG. 8 is a sectional view taken along line of FIG. 6.
Figure 9:
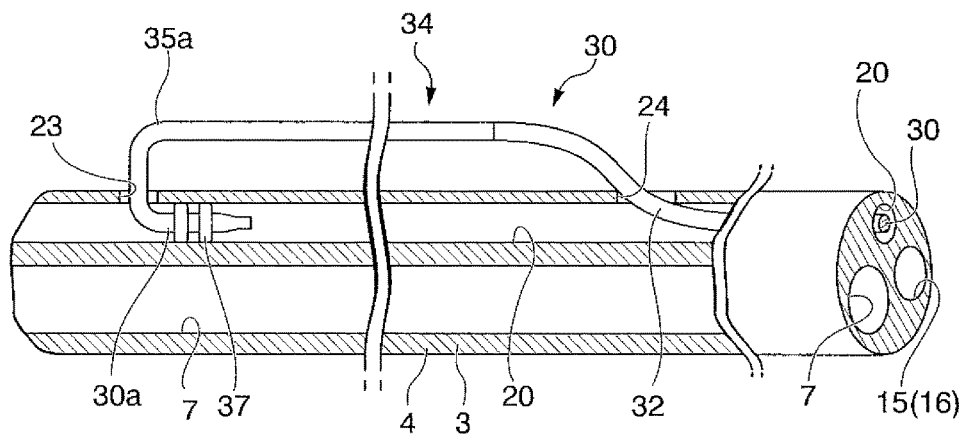
FIG. 9 is a view showing the distal portion of the sheath of the treatment tool for an endoscope according to the first embodiment of the present invention, and is a view which includes a partial sectional view of the sheath when viewed from line IX-IX shown in FIG. 7A.
Figure 10:
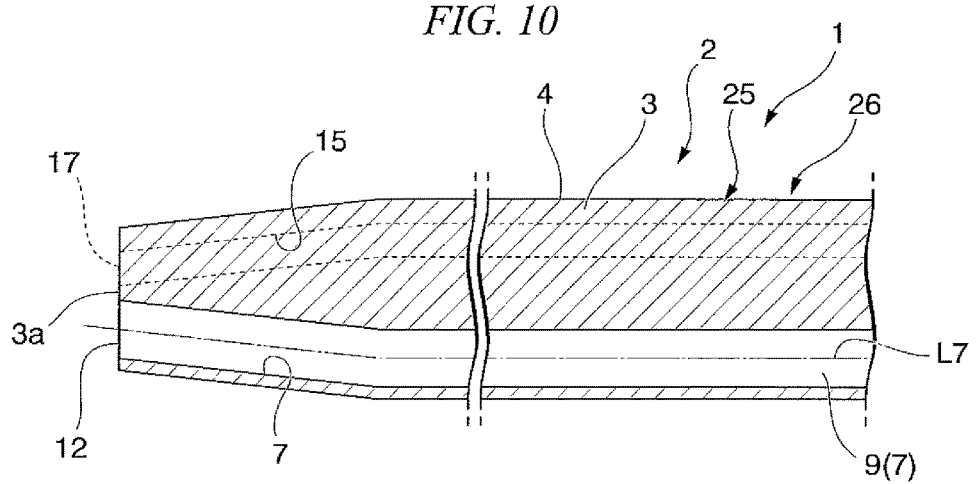
FIG. 10 is a sectional view of the distal end portion of the sheath of the treatment tool for an endoscope according to the first embodiment of the present invention on a first virtual plane.

FIG. 2 is a plan view of the treatment tool 1 for an endoscope. FIG. 3A is a sectional view taken along line of FIG. 2. FIG. 3B is a plan view showing a distal end portion of a sheath 3 of the treatment tool 1 for an endoscope according to the first embodiment of the present invention. FIG. 4 is a sectional view taken along line IV-IV of FIG. 2. FIG. 5 is a perspective view showing a portion of the sheath 3 in the treatment tool 1 for an endoscope. FIG. 6 is a view when the distal portion of the sheath 3 is viewed from a direction perpendicular to a second virtual plane 3. FIG. 7A is a sectional view taken along line of FIG. 6. FIG. 8 is a sectional view taken along line of FIG. 6. FIG. 9 is a view showing the distal portion of the sheath 3, and is a view which includes a partial sectional view of the sheath 3 when viewed from line IX-IX shown in FIG. 7A. FIG. 10 is a sectional view of the distal end portion of the sheath 3 on a first virtual plane α.

The treatment tool 1 for an endoscope includes an insertion portion 2 and an operation portion 40. The insertion portion 2 is an elongated member which is inserted into a treatment tool channel 104 of the endoscope apparatus 100. The insertion portion 2 includes the sheath 3 and a knife wire 30. As shown in FIGS. 1 and 2, the sheath 3 is an elongated member which has a center axis L1 along a longitudinal axis and has flexibility. In the present embodiment, the sheath 3 is formed of a resin.

Hereinafter, the operation portion 40 side of the treatment tool 1 for an endoscope is referred to as a proximal side, and a side on which the insertion portion 2 is provided and which is inserted into the body is referred to as a distal side.

As shown in FIG. 3B, the sheath 3 has a pre-curved portion 4 in a predetermined region including a distal end 3a of the sheath 3. A bending habit is applied to the pre-curved portion 4 so as to be curved in a predetermined direction, and the pre-curved portion 4 has a restoring force which restores the pre-curved portion 4 so as to be a predetermined curved shape. As shown in FIG. 3A, the center axis L1 of the sheath 3 exists in one predetermined plane (hereinafter, referred to as a "first virtual plane α") in the pre-curved portion 4. That is, the pre-curved portion 4 has a restoring force so as to follow the curved shape in which the sheath 3 is curved along the first virtual plane α.

A distal end portion of the pre-curved portion 4 is inserted into a duodenal papilla PV (refer to FIG. 20) of a patient who is an object to be treated. As shown in FIG. 3B, a first distal communication hole 23 and a second distal communication hole 24 described below are disposed at the distal end portion of the pre-curved portion 4.

As shown in FIG. 3A, the configuration of the sheath 3 is described using an orthogonal coordinate system (hereinafter, referred to as a "virtual coordinate system") in which the center axis L1 is an origin, the first virtual plane α is a vertical axis, and a plane (hereinafter, referred to as a "second virtual plane β") orthogonal to the first virtual plane α on the center axis L1 of the sheath 3 is a horizontal axis when a cross section orthogonal to the center axis L1 of the sheath 3 is viewed along the center axis L1 of the sheath 3 from the proximal end 3b of the sheath 3 toward the distal end 3a. In the vertical axis of the virtual coordinate system, the curved direction of the pre-curved portion 4 is referred to as an upper side.

Figure 13A:
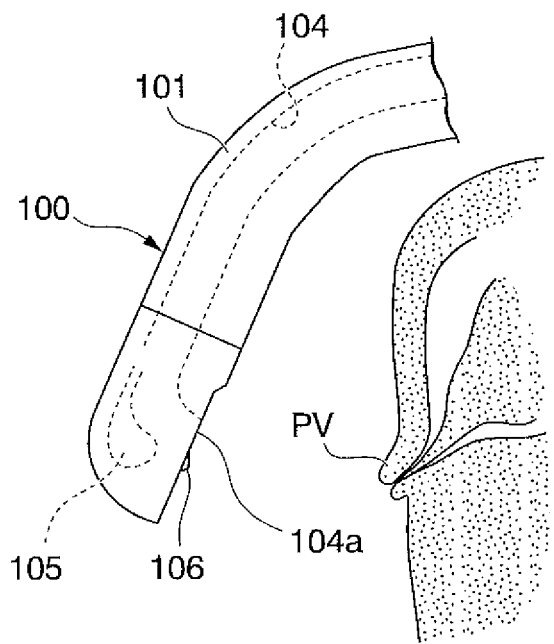
FIG. 13A is a view showing a process when the treatment tool for an endoscope according to the first embodiment of the present invention is used.
Figure 13B:
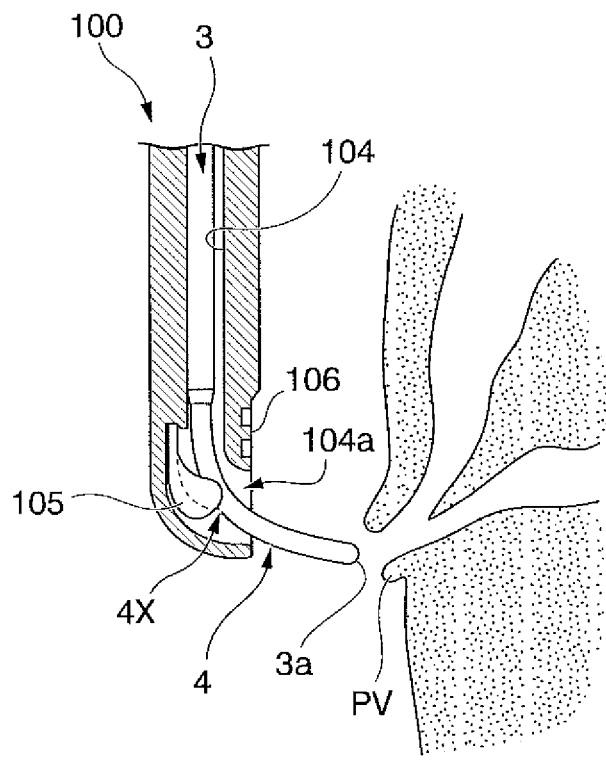
FIG. 13B is a view showing a use aspect of the treatment tool for an endoscope according to the first embodiment of the present invention.

When the distal end of the pre-curved portion 4 protrudes from a distal end 104a of the treatment tool channel 104 of the endoscope apparatus 100, the distal end portion of the pre-curved portion 4 is restored to a curved shape suitable for incision of a target portion to be treated (refer to FIGS. 1 and 13B). As shown in FIGS. 3A and 5, a third lumen (knife wire lumen) 20 is formed inside the sheath 3. The third lumen 20 extends along a longitudinal direction of the sheath 3, and has the center axis which is approximately parallel with the center axis L1 of the sheath 3. In a state where the pre-curved portion 4 is restored to a curved shape, the third lumen 20 is positioned on a region of an inner surface 401 side of the curve in the pre-curved portion 4. Specifically, the third lumen 20 in the pre-curved portion 4 is positioned at a second quadrant Q2 in the virtual coordinate system. That is, as shown in FIG. 3A, when viewed from the viewpoint of a dial plate of a timepiece in which the upper side (the upper side of first virtual plane α) of the vertical axis in the virtual coordinate system of the cross section orthogonal to the center axis L1 of the sheath 3 is set to twelve o'clock, the third lumen 20 in the pre-curved portion 4 is positioned within a range between nine o'clock and twelve o'clock.

As shown FIGS. 3A, 4, and 5, the third lumen 20 is a lumen into which the knife wire 30 described below is inserted. The third lumen 20 is set to a size in which the knife wire 30 can move forward and backward in the third lumen 20. That is, the third lumen 20 has clearance in a state where the knife wire 30 is inserted into the third lumen 20, and the inner diameter of the third lumen 20 is larger than the diameter of the knife wire 30 by the dimensions of the clearance. The third lumen 20 covers the entire outer circumference of the knife wire 30 so as to maintain the knife wire 30 in an electrically insulated state.

As shown in FIG. 7A, the first distal communication hole 23 is open to the outer circumferential surface 3c of the sheath 3, and communicates with the third lumen 20. The first distal communication hole 23 is positioned at the second quadrant Q2 in the virtual coordinate system. That is, when viewed from the viewpoint of a dial plate of a timepiece in which the upper side (the upper side of first virtual plane α) of the vertical axis in the virtual coordinate system of the cross section orthogonal to the center axis L1 of the sheath 3 is set to twelve o'clock, the first distal communication hole 23 is positioned within a range between nine o'clock and twelve o'clock. Specifically, the first distal communication hole 23 communicates with the inner surface 401 (the outer circumferential surface positioned on the inner side of the curved shape) of the curved shape and the third lumen 20 in the pre-curved portion 4. The first distal communication hole 23 is formed so as to be open at the position spaced from the first virtual plane α on the inner surface 401 side of the curved shape in the distal end portion of the pre-curved portion 4. Furthermore, the first distal communication hole 23 is formed so as to be open in the direction spaced from the position of the third lumen 20 toward the outside in the radial direction with respect to the center axis of the sheath 3.

As shown in FIG. 8, the second distal communication hole 24 communicates with the third lumen 20 at a position spaced from the first distal communication hole 23 so as to be closer to the proximal side relative to the first distal communication hole 23 within the region of the distal end portion of the pre-curved portion 4. The second distal communication hole 24 is positioned at the second quadrant Q2 in the virtual coordinate system. That is, similarly to the first distal communication hole 23, the second distal communication hole 24 communicates with the inner surface 401 of the curve (the outer circumferential surface positioned on the inner side of the curved shape) and the third lumen 20 in the pre-curved portion 4. Furthermore, the second distal communication hole 24 is formed so as to be open at the position spaced from the first virtual plane α on the inner surface 401 side of the curved shape in the distal end portion of the pre-curved portion 4. Moreover, the second distal communication hole 24 is formed so as to be open in the direction spaced from the position of the third lumen 20 toward the outside in the radial direction with respect to the center axis of the sheath 3. Furthermore, in the cross section orthogonal to the center axis L1 of the sheath 3, preferably, the positions of the second distal communication hole 24 and the first distal communication hole 23 in the circumferential direction of the sheath 3 coincide with each other. Moreover, the positions of the first distal communication hole 23 and the second distal communication hole 24 in the circumferential direction with the center axis L1 of the sheath 3 as a center do not necessarily need to coincide with each other, and the first distal communication hole 23 and the second distal communication hole 24 may be disposed so as to be separated from each other by a predetermined angle in the circumferential direction.

The first distal communication hole 23 and the second distal communication hole 24 can exert the functions if the holes 23 and 24 are provided so as to communicate with the inner surface 401 of the curved shape and the third lumen 20 in the pre-curved portion 4, and are open in the direction spaced from the center axis L1 of the sheath 3 toward the outside in the radial direction of the third lumen 20 at the position spaced from the first virtual plane α on the inner surface 401 side of the curved shape in the distal end portion of the pre-curved portion 4.

As shown in FIGS. 6 and 9, the knife wire 30 includes a cutting portion 34 which incises a target portion to be treated. The knife wire 30 includes a distal fixing member (fixing portion) 37 at the distal end thereof. The cutting portion 34 protrudes from the first distal communication hole 23 and the second distal communication hole 24, extends between the first distal communication hole 23 and the second distal communication hole 24, and is provided so as to incise tissues. In order to prevent excessive incision, as shown in FIGS. 6 and 8, the knife wire 30 may include an insulating film 32 which covers a core wire 31 having conductivity.

For example, the insulating film 32 is formed by coating or covering resins such as polytetrafluoroethylene (PTFE), tetrafluoroethylene-hexafluoropropylene resin (FEP), polyethylene, polyolefin, polyamide, vinyl chloride, latex, natural rubber, polysulfone, polyphenylsulfon, polyetherimide, POM, PEEK, polycarbonate, or ABS, or combined resin materials thereof on the outer surface of the core wire 31.

As shown in FIG. 6, the cutting portion 34 is a portion in which the core wire 31 is not covered on the insulating film 32 over the entire length of the knife wire 30, and which protrudes toward the outside of the sheath 3 via the first distal communication hole 23 and the second distal communication hole 24. The cutting portion 34 can incise biological tissues by energizing a high-frequency current supplied to the core wire 31 via a connector 73 described below. The cutting portion 34 includes a curved knife portion 35 and a bending portion 36.

The proximal end of the knife wire 30 is fixed to a slider portion 71 of a handle portion 67 in the operation portion 40 (refer to FIG. 2). As shown in FIGS. 5 to 9, the knife wire 30 is inserted into the third lumen 20. As shown in FIG. 9, the distal end of the knife wire 30 is positioned in the vicinity of the first distal communication hole 23, and the distal end of the knife wire 30 is fixed to the third lumen 20 by the distal fixing member 37.

Specifically, the distal fixing member 37 is fixed to the distal end 30a of the knife wire 30, and is fixed to the inner portion of the third lumen 20. That is, in the state where the distal fixing member 37 is inserted into the pre-curved portion 4, the knife wire 30 and the pre-curved portion 4 are fixed to each other. Furthermore, the distal fixing member 37 is connected to an inner circumferential surface of the third lumen 20 in the pre-curved portion 4 by friction, bonding, or other connection methods. Since the distal fixing member 37 is fixed to the inner portion of the third lumen 20 (pre-curved portion 4), the distal portion of the knife wire 30 is not extracted from the first distal communication hole 23.

Since the knife wire 30 is fixed to the pre-curved portion 4, if the knife wire 30 is pulled toward the proximal end side, the pre-curved portion 4 in the vicinity in which the first distal communication hole 23 is provided is pulled toward the proximal end side, and the pre-curved portion 4 is curved so as to be larger than a curved shape applied in advance. That is, the knife wire 30 has a function of curving the distal end side of the pre-curved portion 4 to be equal to or more than a curved angle applied in advance, besides to the function of incising the target portion to be treated.

As shown in FIG. 6, the curved knife portion 35 is positioned so as to be exposed from the inner surface 401 of the curved shape of the pre-curved portion 4 in a region between the first distal communication hole 23 and the second distal communication hole 24. The bending portion 36 is disposed at the distal end 35a of the curved knife portion 35. In the curved knife portion 35, when viewed in the vertical axis direction on the first virtual plane $\alpha$ in the virtual coordinate system, a maximum portion 35c is formed between the first distal communication hole 23 and the second distal communication hole 24. The maximum portion 35c of the curved knife portion 35 has a curved shape which is disposed across a portion of the pre-curved portion 4 between the first distal communication hole 23 and the second distal communication hole 24 at a position spaced from the first virtual plane $\alpha$. The maximum portion 35c of the curved knife portion 35 is positioned at a position close to the first distal communication hole 23 from the center between the first distal communication hole 23 and the second distal communication hole 24 in the center axis L1 direction of the sheath 3.

As shown in FIG. 7A, the bending portion 36 has a shape in which the knife wire 30 protruding from the first distal communication hole 23 is bent with respect to the protrusion direction from the first distal communication hole 23 in the direction approximately parallel with a tangential line to the outer circumferential surface 3c of the sheath 3 at the second quadrant Q2 in the virtual coordinate system defined by the first virtual plane $\alpha$ and the second virtual plane $\beta$. Specifically, the bending portion 36 is positioned at the position protruding from the first distal communication hole 23, and has a shape which is bent in the direction of enlarging a space from the first virtual plane $\alpha$ against the direction in which the first distal communication hole 23 is open.

The bending portion 36 is a portion in which the core wire 31 is bent such that the core wire 31 extending from the curved knife portion 35 toward the distal end 30a of the knife wire 30 is curved toward the first distal communication hole 23. The bending portion 36 may be covered with the insulating film 32.

The curved knife portion 35 is curved so as to reach the second distal communication hole 24 from the first distal communication hole 23 on a virtual plane which is approximately parallel with a tangential plane which intersects a first virtual plane $\alpha$ within the range of the second quadrant Q2 and comes into contact with the outer circumferential surface 3c of the sheath 3 in the virtual coordinate system defined by the first virtual plane $\alpha$ and the second virtual plane $\beta$, and the curved knife portion 35 is curved such that the maximum portion 35c is separated farthest from the first virtual plane $\alpha$ at the curved knife portion 35.

For example, the maximum portion 35c may be curved so as to be inclined with respect to the first virtual plane $\alpha$ and the second virtual plane $\beta$ such that the maximum portion 35c approaches the second virtual plane $\beta$ as the maximum portion 35c is spaced from the bending portion 36 toward the proximal side. The maximum portion 35c may be curved so as to be inclined with respect to the first virtual plane $\alpha$ and the second virtual plane $\beta$ such that the maximum portion 35c is spaced from the second virtual plane $\beta$ as the maximum portion 35c is spaced from the bending portion 36. The maximum portion 35c may extend so as to be approximately parallel with the second virtual plane $\beta$.

Figure 7B:
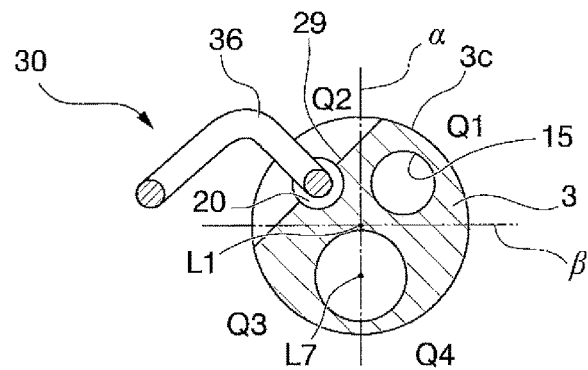
FIG. 7B shows a modification example of the sheath of the treatment tool for an endoscope according to the first embodiment of the present invention, and is a sectional view at the same position as line XII-XII of FIG. 6.

Instead of the above-described configuration, as shown in FIG. 7B, the first distal communication hole 23 may also be formed so as to be notched from the outer circumferential surface 3c of the pre-curved portion 4 at the position of the inner surface 401 of the curved shape in the pre-curved portion 4 (sheath 3). Specifically, the first distal communication hole 23 may be a notch portion 29 which is notched so as to communicate with the third lumen 20 from the circumferential surface 3c of the pre-curved portion 4 at the position of the second quadrant (between nine o'clock and twelve o'clock). Similarly to the first distal communication hole 23, the second distal communication hole 24 may also be formed so as to be notched from the outer circumferential surface 3c of the pre-curved portion 4 at the position of the inner surface 401 of the curved shape in the pre-curved portion 4 (sheath 3). Specifically, the second distal communication hole 24 may be the notch portion 29 which is notched so as to communicate with the third lumen 20 from the circumferential surface 3c of the pre-curved portion 4 at the position of the second quadrant (between nine o'clock and twelve o'clock).

As shown in FIG. 6, preferably, the direction of the longitudinal axis of the core wire 31 at the distal end 35a of the curved knife portion 35 is a direction along the surface orthogonal to the center axis L1 of the sheath 3. In addition, the direction of the distal end 35a of the curved knife portion 35 may be a direction toward the proximal side of the sheath 3 slightly away from the surface orthogonal to the center axis L1 (longitudinal axis of the sheath 3) of the sheath 3.

As shown in FIGS. 3A, and 7A to 10, besides to the third lumen 20, a first lumen 7 and a second lumen 15 are formed inside the sheath 3. The first lumen 7 and the second lumen 15 are formed to extend so as to be parallel with one another in a longitudinal direction of the sheath 3.

In a case where the first lumen 7 and the second lumen 15 are provided in addition to the third lumen 20, preferably, the second lumen 15 and the third lumen 20 are positioned in a region on the inner surface 401 side of the curve. It is preferable that the first lumen 7 is positioned in a region on an outer surface 402 side of the curve.

In the present embodiment, as shown in FIG. 3A, preferably, the first virtual plane $\alpha$ is set to a position which crosses a wall portion 3d which is positioned between the second lumen 15 and the third lumen 20 in the sheath 3. That is, as shown in FIG. 3A, the second lumen 15 and the third lumen 20 are positioned on both sides in the state where the first virtual plane $\alpha$ is interposed therebetween. Specifically, the third lumen 20 is positioned at the second quadrant Q2 in the above-described virtual coordinate system, the second lumen 15 is positioned at a first quadrant Q1 in the above-described virtual coordinate system, and the wall portion 3d is positioned on the first virtual plane $\alpha$. A center axis L7 of the first lumen 7 is positioned on the first virtual plane $\alpha$, and preferably, is positioned below the center axis L1 of the sheath 3, that is, between a third quadrant Q3 and a fourth quadrant Q4 of the virtual coordinate system. That is, the first lumen 7 is configured such that the center axis L7 of the first lumen 7 is curved on the first virtual plane α and the first virtual plane α is positioned so as to cross the inner wall of the first lumen 7. As a result, the first virtual plane α crosses the inner space of the first lumen 7.

As shown in FIGS. 3A and 10, the first lumen 7 includes an outlet portion 12 which is open to the distal end 3a, a guide wire accommodation portion 9, and an inlet portion 8 which is open to the proximal end side. The outlet portion 12 communicates with the guide wire accommodation portion 9. The first lumen 7 has an inner diameter which allows the guide wire 80 to move forward and backward in the first lumen 7, and may be used as a passage through which the guide wire can move. That is, the first lumen 7 is a lumen in which the guide wire 80 is held in the inner portion. In the present embodiment, the case where the first lumen 7 is used as the passage through which the guide wire moves is exemplified. However, the present invention is not limited to the guide wire, and the first lumen 7 may be used as a passage through which other treatment tools move.

The second lumen 15 extends from the proximal end 3b (refer to FIG. 2) of the sheath 3 to the distal end 3a (FIGS. 2 and 3A) of the sheath 3. For example, the second lumen 15 may be used as a liquid-feeding lumen for feeding liquid such as a contrast agent. The second lumen 15 can be used as a liquid-discharging lumen for removing liquid in the body.

A second port 62 (refer to FIG. 12A) described below is provided at the proximal end of the second lumen 15. The second port 62 has an opening through which liquid is introduced. The distal end of the second lumen 15 has an opening through which the liquid introduced from the second port 62 is discharged.

Figure 11:
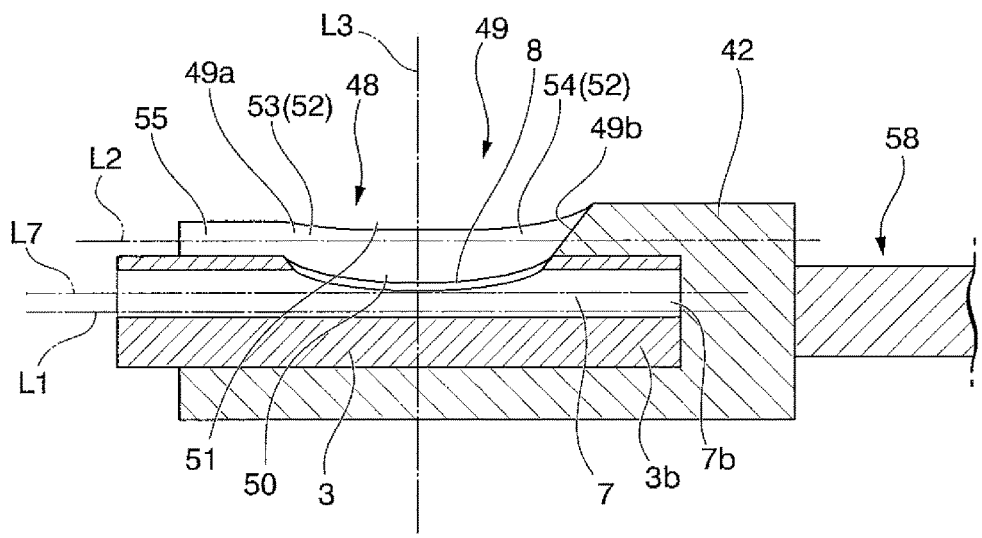
FIG. 11 is a sectional view showing a first port portion of the treatment tool for an endoscope according to the first embodiment of the present invention.

As shown in FIG. 2, the operation portion 40 is a portion which is held by an operator, and is disposed at the proximal end 2b (proximal end 3b of sheath 3) of the insertion portion 2. Various operations for operating the treatment tool 1 for an endoscope are input to the operation portion 40. The operation portion 40 includes a distal configuration portion 41, a proximal configuration portion 61, and the handle portion 67. The distal configuration portion 41 includes a main body portion 42, a connection portion 45 with respect to the endoscope apparatus 100, and a connection portion 48 with respect to the sheath 3. The main body portion 42 is a hard member, and as shown in FIGS. 11 and 12A, the main body portion 42 is connected to a first port 49 described below in the connection portion 48.

Figure 12A:
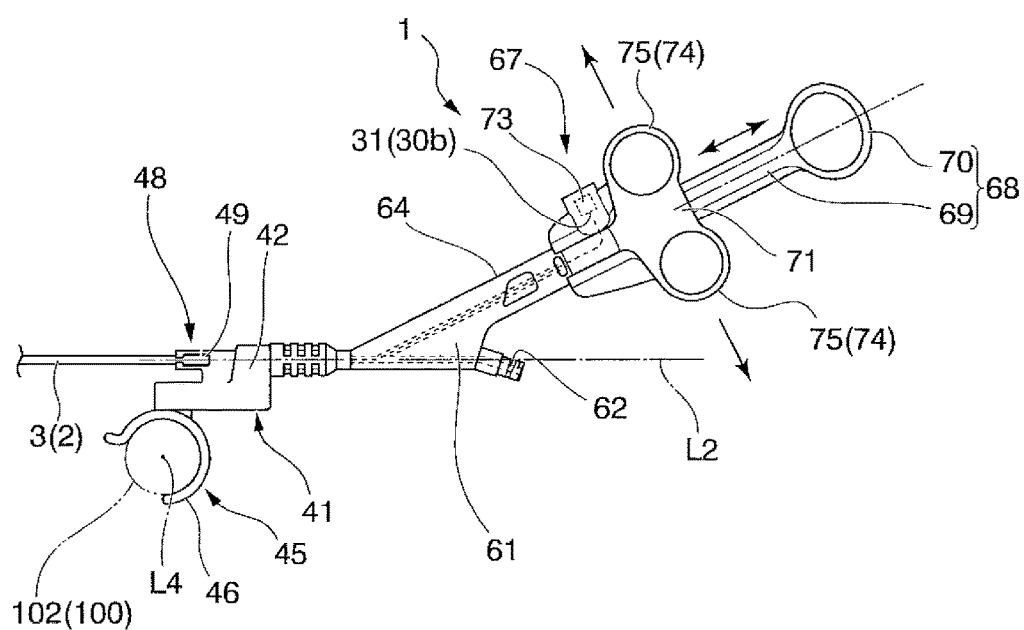
FIG. 12A is a view showing a positional relationship between a hook and the first port in a state where the treatment tool for an endoscope according to the first embodiment of the present invention is attached to an endoscope apparatus.

As shown in FIG. 12A, the connection portion 45 has a hook 46. The hook 46 is a locking portion which can be locked to the holding portion 102 which is provided in the endoscope apparatus 100.

As shown in FIG. 2, inputs for operating the knife wire 30 are applied to the handle portion 67 of the proximal configuration portion 61 by an operator. The handle portion 67 includes a shaft portion 68 and a slider portion 71. The shaft portion 68 is fixed to a handle-fixing portion 64. The handle-fixing portion 64 is connected to the distal configuration portion 41. The slider portion 71 is slidably connected along the longitudinal axis of the shaft portion 68.

The shaft portion 68 includes a rod-shaped portion 69 and a ring portion 70. The rod-shaped portion 69 extends so as to be coaxial with a center axis L5 of the handle-fixing portion 64 or so as to be linear along the center axis L5 of the handle-fixing portion 64. The ring portion 70 is an annular portion through which fingers of an operator can pass. The ring portion 70 is formed at the proximal end of the rod-shaped portion 69.

The slider portion 71 may include a connector 73 which can be connected to a high-frequency power supply device and a finger-hooking portion 74. Two rings 75 through which fingers of an operator can pass are formed at the finger-hooking portion 74.

The proximal end of the knife wire 30 is electrically connected to the connector 73.

Fingers of an operator pass through the two rings 75 and the ring portion 70, and thus, the finger-hooking portion 74 can be used to move the knife wire 30 forward and backward by opening and closing operations of the hands of the operator.

Next, the operation of the treatment tool 1 for an endoscope according to the present embodiment will be described. FIG. 13A is a view showing a process when the treatment tool 1 for an endoscope is used.

As shown in FIGS. 1 and 13A, in the present embodiment, a side view type endoscope apparatus 100 which is suitable for observing a duodenal papilla PV is used. For example, the side view type endoscope apparatus 100 includes a tubular member 101, a holding portion 102, a treatment tool channel port 103, a treatment tool channel 104, a raising stand 105, and an imaging portion 106. The tubular member 101 is a portion which is inserted into the body. The holding portion 102 is disposed at the proximal end of the tubular member 101. The treatment tool channel port 103 is disposed on a portion of the holding portion 102. The treatment tool channel 104 communicates with the treatment tool channel port 103 and is disposed inside the tubular member 101. The raising stand 105 is provided so as to be movable in an opening portion from which the treatment tool protrudes in order to change the direction of the treatment tool or the like protruding from the treatment tool channel 104 at the distal end 104a of the treatment tool channel 104 to the direction orthogonal to the center axis of the tubular member 101. The imaging visual field of the imaging portion 106 faces the direction orthogonal to the center axis of the tubular member 101. The imaging portion 106 is provided so as to be adjacent to the opening portion from which the treatment tool protrudes.

The side view type endoscope apparatus 100 according to the present embodiment includes a bendable portion 107 (refer to FIG. 1.). The bendable portion 107 is bently operated by a bending operation section 107a. The bendable portion 107 actively bendy deforms a treatment tool channel which is disposed in an endoscope insertion portion which is inserted into the body.

First, as shown in FIG. 13A, an operator guides the endoscope apparatus 100 to the duodenal papilla PV which is the target portion to be treated and observes the target portion to be treated using the endoscope apparatus 100.

Figure 12B:
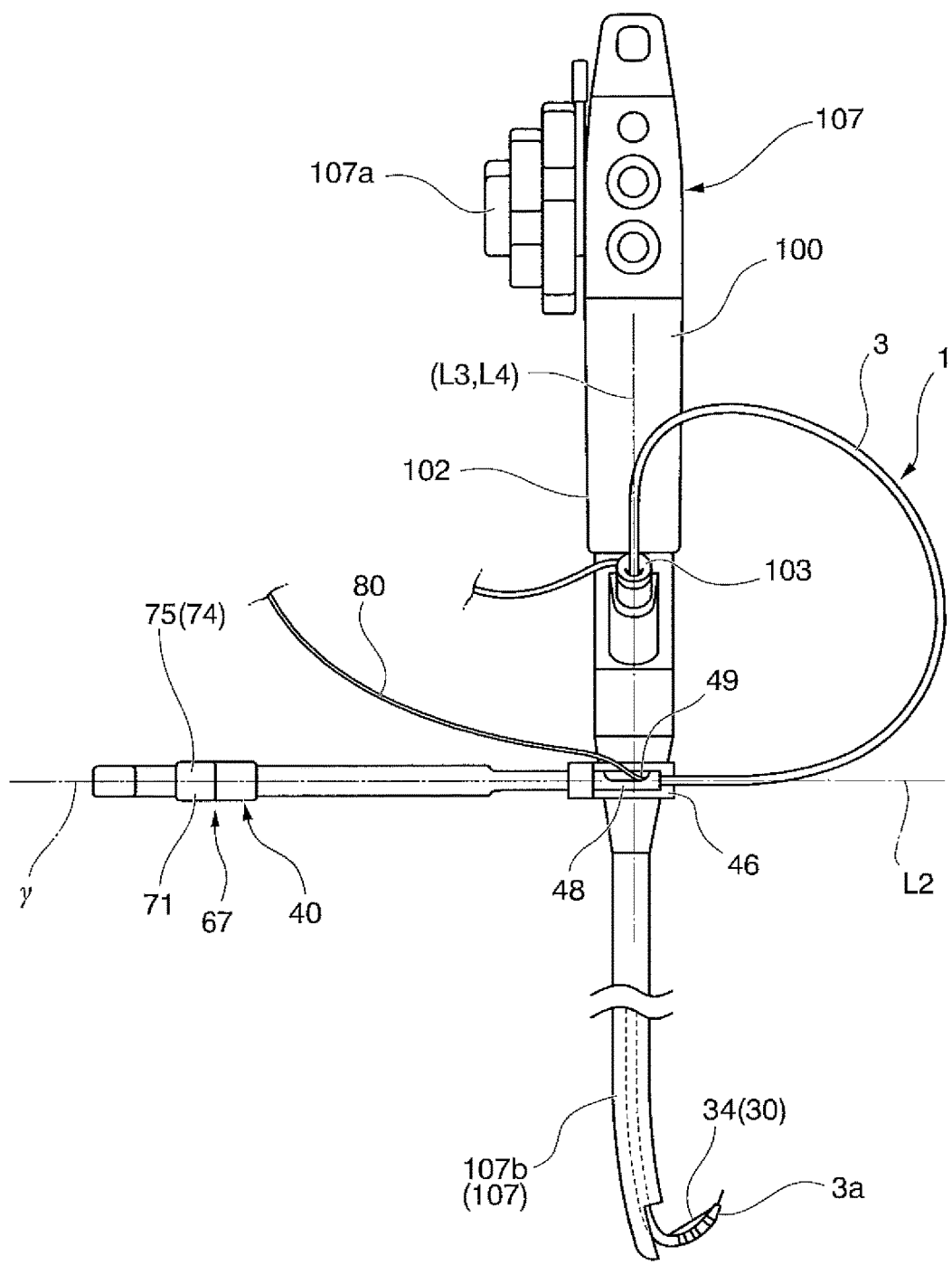
FIG. 12B is a view showing a positional relationship between the first port and an operation portion in a state where the treatment tool for an endoscope according to the first embodiment of the present invention is attached to the endoscope apparatus.

After the target portion to be treated is observed, the treatment tool 1 of an endoscope is inserted into the treatment tool channel 104 of the endoscope apparatus 100. As shown in FIG. 12B, the operation portion 40 of the treatment tool 1 for an endoscope is connected to the endoscope apparatus 100 via the hook 46. Accordingly, for example, an operator of the treatment tool 1 for an endoscope can extract and input the sheath 3 with respect to treatment tool channel port 103 of the endoscope apparatus 100 in a state of holding the endoscope apparatus 100 by the left hand and the sheath 3 by the right hand.

Figure 14A:
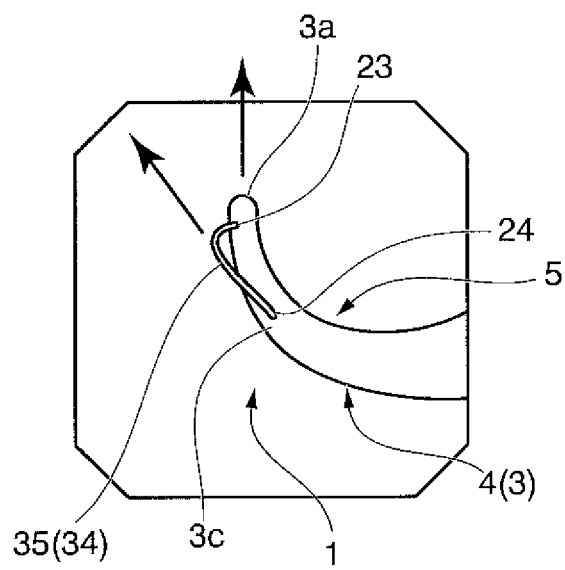
FIG. 14A is a schematic view showing the treatment tool for an endoscope which is reflected on an endoscopic image which is imaged using the endoscope apparatus according to the first embodiment of the present invention.

FIG. 13B is a view showing a process in which the treatment tool 1 for an endoscope is used. FIG. 14A is a schematic view showing the treatment tool 1 for an endoscope according to the present embodiment which is reflected on an endoscopic image which is imaged using the endoscope apparatus 100.

As shown in FIG. 13B, the sheath 3 is operated by an operator, the distal end 3a of the sheath 3 protrudes from the distal end 104a (opening portion) of the treatment tool channel 104, and as shown in FIG. 14A, imaging is performed by the imaging portion 106 of the endoscope apparatus 100.

In a case where endoscopic sphincterotomy (EST) is performed at the duodenal papilla PV using the side view type endoscope apparatus 100, when the image captured by the endoscope apparatus 100 is viewed from the viewpoint of a dial plate of a timepiece in which the upper center of the image is set to twelve o'clock, the direction of the imaging portion is adjusted such that the incision target portion of the duodenal papilla PV is reflected between eleven o'clock and twelve o'clock in the image captured by the endoscope apparatus 100. In this state, by incising the duodenal papilla PV such that the duodenal papilla PV is expanded from the opening portion of the duodenal papilla PV, a passage through which a calculus or the like in the duodenal papilla PV passes is formed.

In order to perform the above-described EST, first, an operator passes the pre-curved portion 4 of the treatment tool 1 of an endoscope through the treatment tool channel 104 which is bent by the bendable portion 107 of the endoscope apparatus 100. At this time, since the curved shape is applied to the pre-curved portion 4 in advance, until the curved shape of the pre-curved portion 4 follows the curved shape of the treatment tool channel 104 inside the treatment tool channel 104 bent by the bendable portion 107 or the raising stand 105, the pre-curved portion 4 is passively rotated with the center axis L1 of the sheath 3 as a rotation center. Thereafter, the operator protrudes the distal end of the pre-curved portion 4 from the distal end 104a of the treatment tool channel 104 of the endoscope apparatus 100.

Figure 14B:
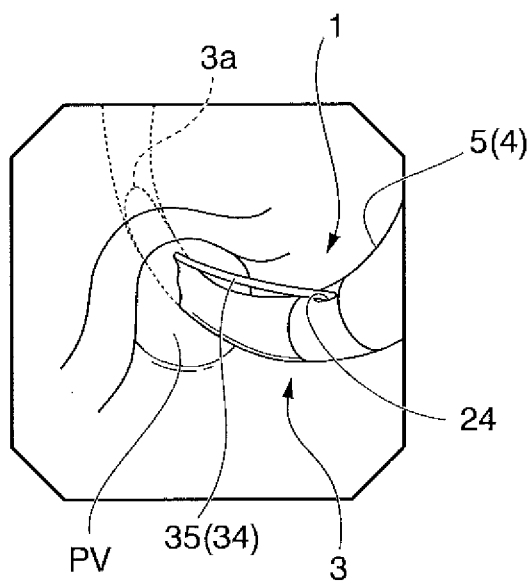
FIG. 14B is a schematic view showing an endoscopic image in a process of treatment using the treatment tool for an endoscope according to the first embodiment of the present invention.

Subsequently, as shown in FIG. 14A, the distal end portion of the pre-curved portion 4 is operated to enter an imaging visual field of the imaging portion 106 of the endoscope apparatus 100. At this time, the first distal communication hole 23 and the second distal communication hole 24 are provided so as to be open to the outer circumferential surface 3c of the pre-curved portion 4 at the position of the inner surface 401 of the curve in the pre-curved portion 4, and since the first distal communication hole 23 and the second distal communication hole 24 are open to the direction spaced from the outside in the radial direction from the third lumen 20 with respect to the center axis L1 of the sheath 3, if the distal end 3a of the sheath 3 is directed to the twelve o'clock direction, the cutting portion 34 is slightly directed to eleven o'clock. Due to the pre-curved portion 4 to which the curved shape is applied along the first virtual plane α and the bending portion 36 which is bent in the direction spaced from the first virtual plane α in the direction in which the first distal communication hole 23 is open, if the distal end 3a of the sheath 3 is directed to the twelve o'clock direction, the cutting portion 34 is slightly directed to eleven o'clock. That is, as shown in FIG. 14B, the longitudinal axis of the cutting portion 34 is approximately parallel with the direction in which a conduit line of a bile duct extends. Accordingly, even if the sheath 3 is not positively rotated with the center axis L1 of the sheath 3 as a rotation center such that the cutting portion 34 is directed to eleven o'clock, it is possible to passively rotate the cutting portion 34 so as to be directed to eleven o'clock.

As described above, in the case where the treatment tool 1 of an endoscope according to the present embodiment is applied to the side view type endoscope apparatus 100 to incise the duodenal papilla PV, it is possible to easily incise a tissue (a position with little bleeding) in the direction in which the conduit line of the bile duct extends.

(First Modification Example)

Figure 15A:
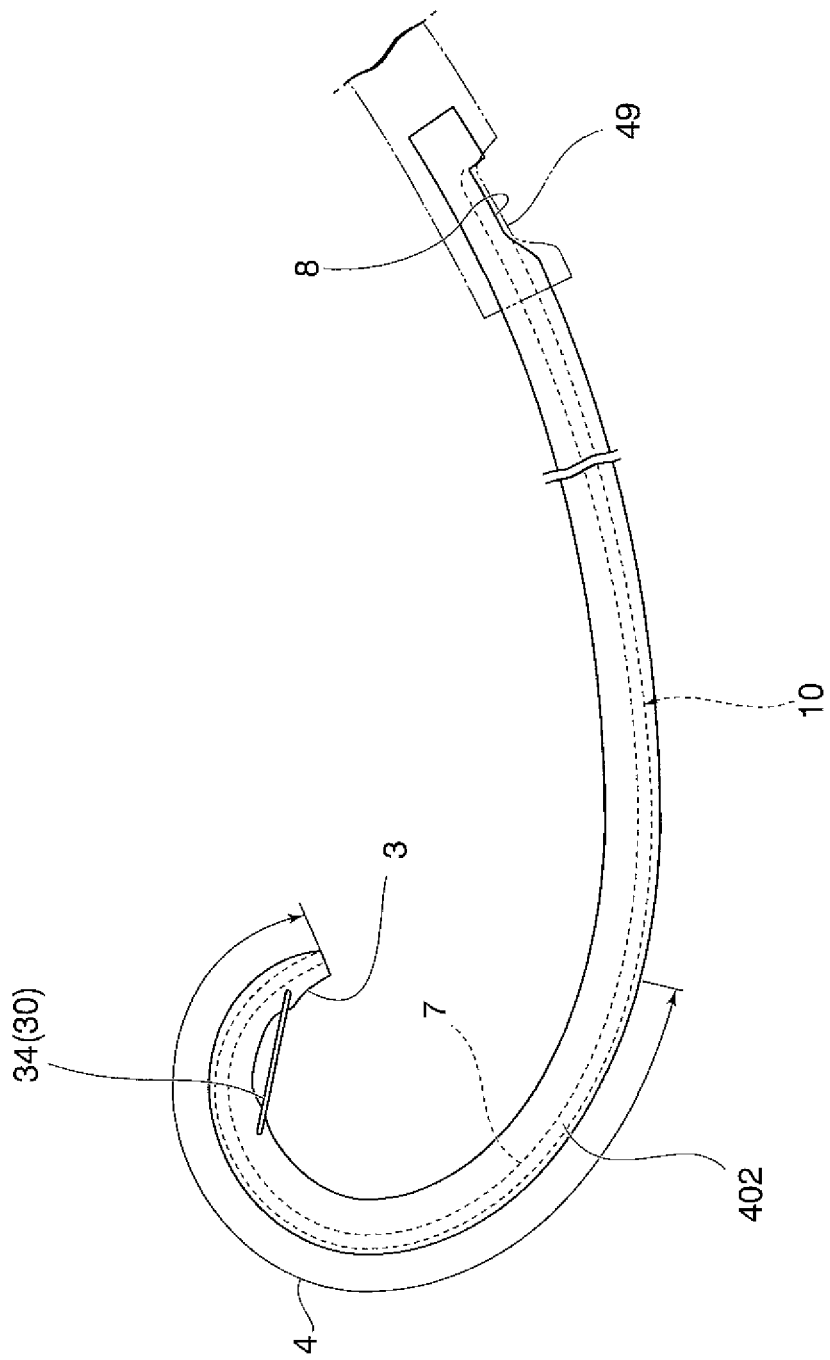
FIG. 15A is a plan view showing a sheath of a first modification example of the first embodiment.
Figure 15B:
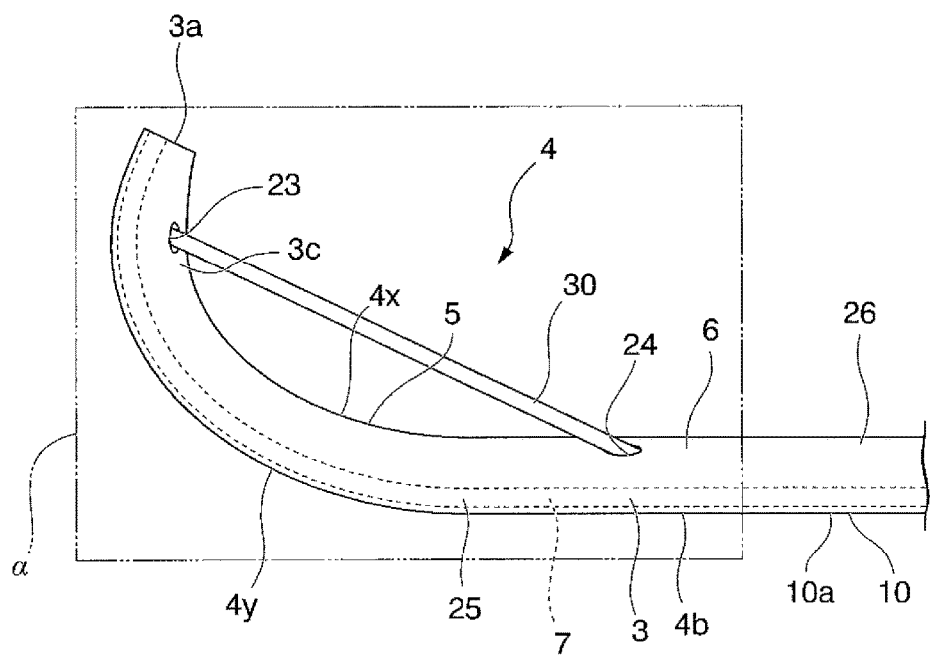
FIG. 15B is a plan view showing the distal end portion of the sheath of the first modification example of the first embodiment.
Figure 15C:
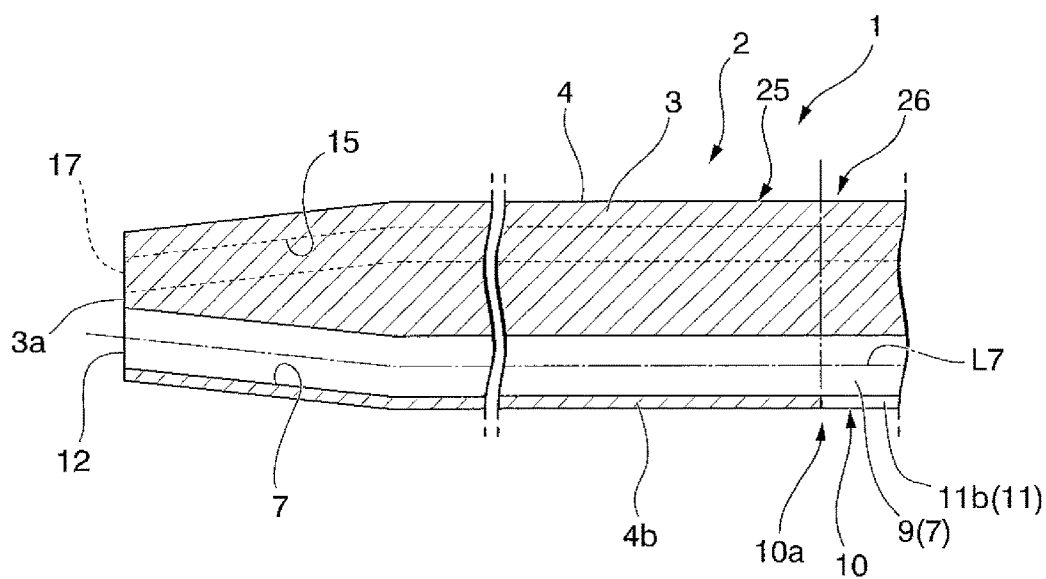
FIG. 15C is a sectional view showing the distal end portion of the sheath of the first modification example of the first embodiment on the first virtual plane.

Hereinafter, modifications of the treatment tool 1 of an endoscope according to the present embodiment will be described. In the following descriptions, the same reference numerals are assigned to configurations common to the above-described configurations, and overlapping descriptions thereof are omitted. FIG. 15A is a plan view showing the sheath 3 of the present modification example. FIG. 15B is a plan view showing the distal end portion of the sheath 3 of the present modification example. FIG. 15C is a sectional view showing the distal end portion of the sheath 3 of the present modification example on the first virtual plane α.

In the present modification example, as shown in FIG. 15A, the first lumen 7 further includes a slit portion 10.

Figure 16:
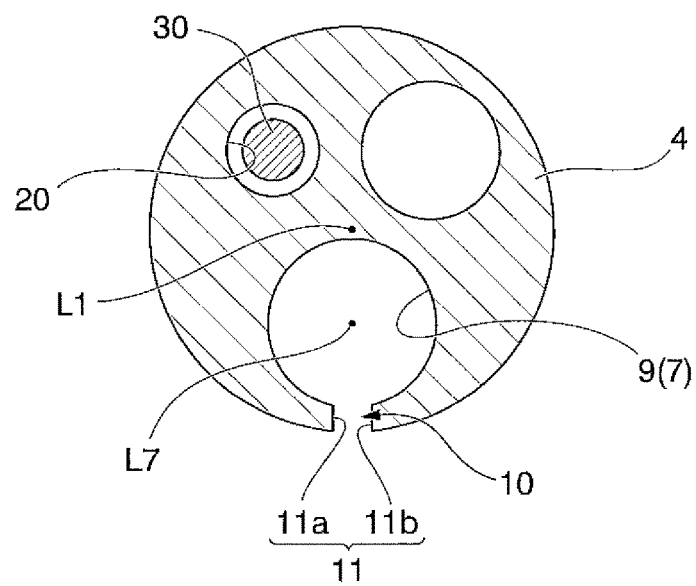
FIG. 16 is a sectional view showing the sheath of the first modification example of the first embodiment.
Figure 17:
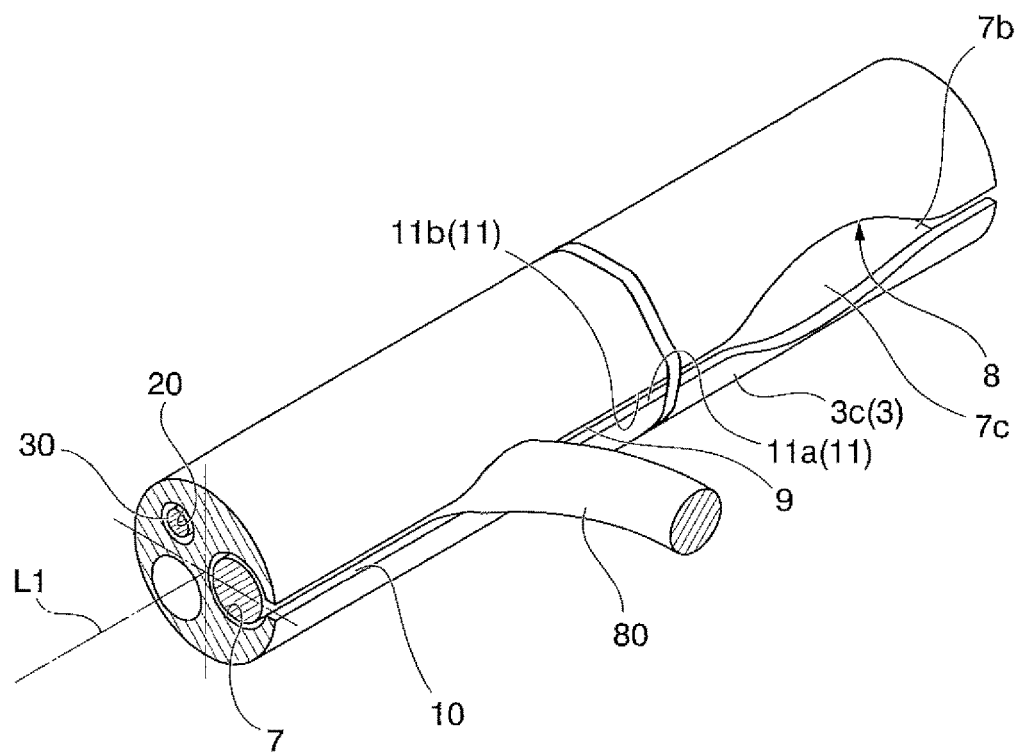
FIG. 17 is a perspective view showing a portion of the sheath of the first modification example of the first embodiment.

As shown in FIGS. 16 and 17, the slit portion 10 is an elongated notch which is open to the outer circumferential surface 3c of the sheath 3 such that the first lumen 7 communicates with the outside of the sheath 3, and which is formed so as to extend in the center axis L1 direction of the sheath 3. The slit portion 10 has a shape in which a resin member configuring the sheath 3 is cut out in the center axis L1 direction of the sheath 3. The slit portion 10 is formed along the center axis L1 of the sheath 3 at a position at which the outer circumferential surface of the pre-curved portion 4 and the predetermined first virtual plane α intersect each other in the region around the proximal end 4b of the pre-curved portion 4. The slit portion 10 extends to the inlet portion 8. In the pre-curved portion 4, the position of the distal end 10a of the slit portion 10 is positioned so as to be closer to the proximal end relative to the second communication hole 24 (refer to FIGS. 15A to 15C).

As shown in FIG. 16, the slit portion 10 has a pair of flap portions 11 (first flap 11a and second flap 11b) which are disposed so as to be spaced from each other such that an opening width of the slit portion 10 is smaller than the diameter of the guide wire 80. The flap portions 11 are a pair of elastic portions which covers the guide wire accommodation portion 9 by a resin member configuring the sheath 3. The flap portions 11 are deformed until a gap is generated, which has a size by which the guide wire 80 can pass through by force of an operator when the guide wire 80 is detached from the guide wire accommodation portion 9 through the slit portion 10.

As shown in FIG. 17, the inlet portion 8 is a portion which is open to the outer circumferential surface 3c of the sheath 3 so as to have the same size as the diameter of the guide wire 80 or to have a larger size than the diameter of the guide wire 80 in the vicinity of a proximal end 7b of the first lumen 7. In other words, the inlet portion 8 is an opening portion in which an inner surface 7c of the first lumen 7 is exposed to the outside in a state where the flap portions 11 described below are not provided, and which has a wider width than that of the slit portion 10.

The length of the inlet portion 8 in the center axis L1 direction of the sheath 3 is larger than the inner diameter of the guide wire accommodation portion 9 in the first lumen 7. That is, the inlet portion 8 has a long hole shape which is long in the center axis L1 direction of the sheath 3.

As shown in FIG. 16, the guide wire accommodation portion 9 has a circular contour except for a boundary between the guide wire accommodation portion 9 and the slit portion 10 in the cross section orthogonal to the center axis L1 of the sheath 3. That is, the guide wire accommodation portion 9 has an approximately C-shaped contour shape in the cross section orthogonal to the center axis L1 of the sheath 3. The guide wire accommodation portion 9 has clearance in a state where the guide wire 80 is inserted into the guide wire accommodation portion 9 such that the guide wire 80 can move forward and backward, and the inner diameter of the guide wire accommodation portion 9 is larger than the diameter of the guide wire 80 by the dimensions of the clearance. Moreover, in the present modification example, it is exemplified that the guide wire accommodation portion 9 has an approximately C-shaped contour in the cross section orthogonal to the center axis L1 of the sheath 3. However, the present invention is not limited to the C shape, and may be a U shape.

Figure 18:
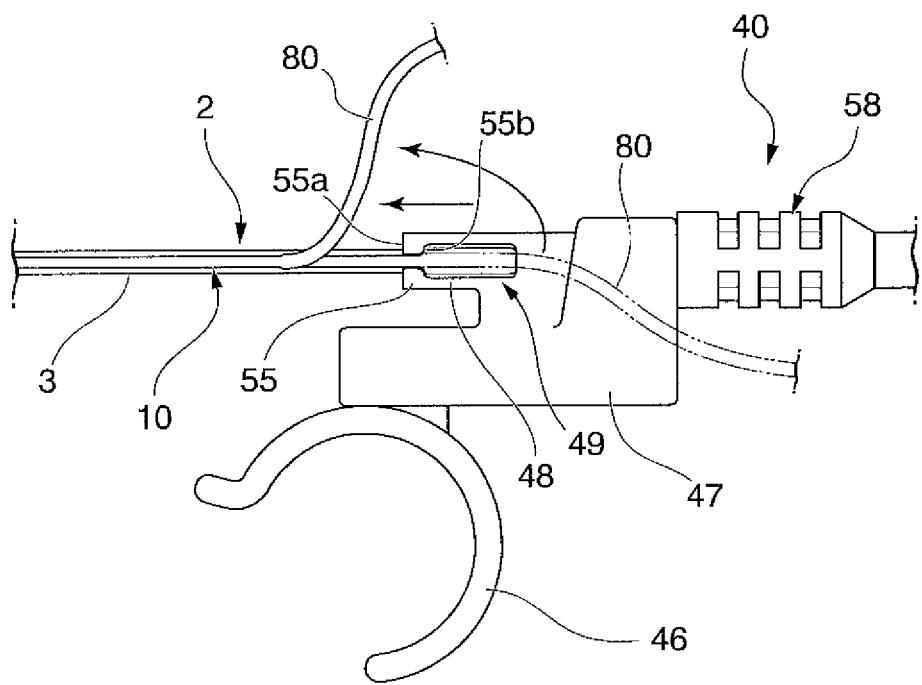
FIG. 18 is a view showing a process in which the treatment tool for an endoscope is removed from the endoscope apparatus in a state where a guide wire which is attached to the treatment tool for an endoscope according to the first modification example of the first embodiment remains.
Figure 19:
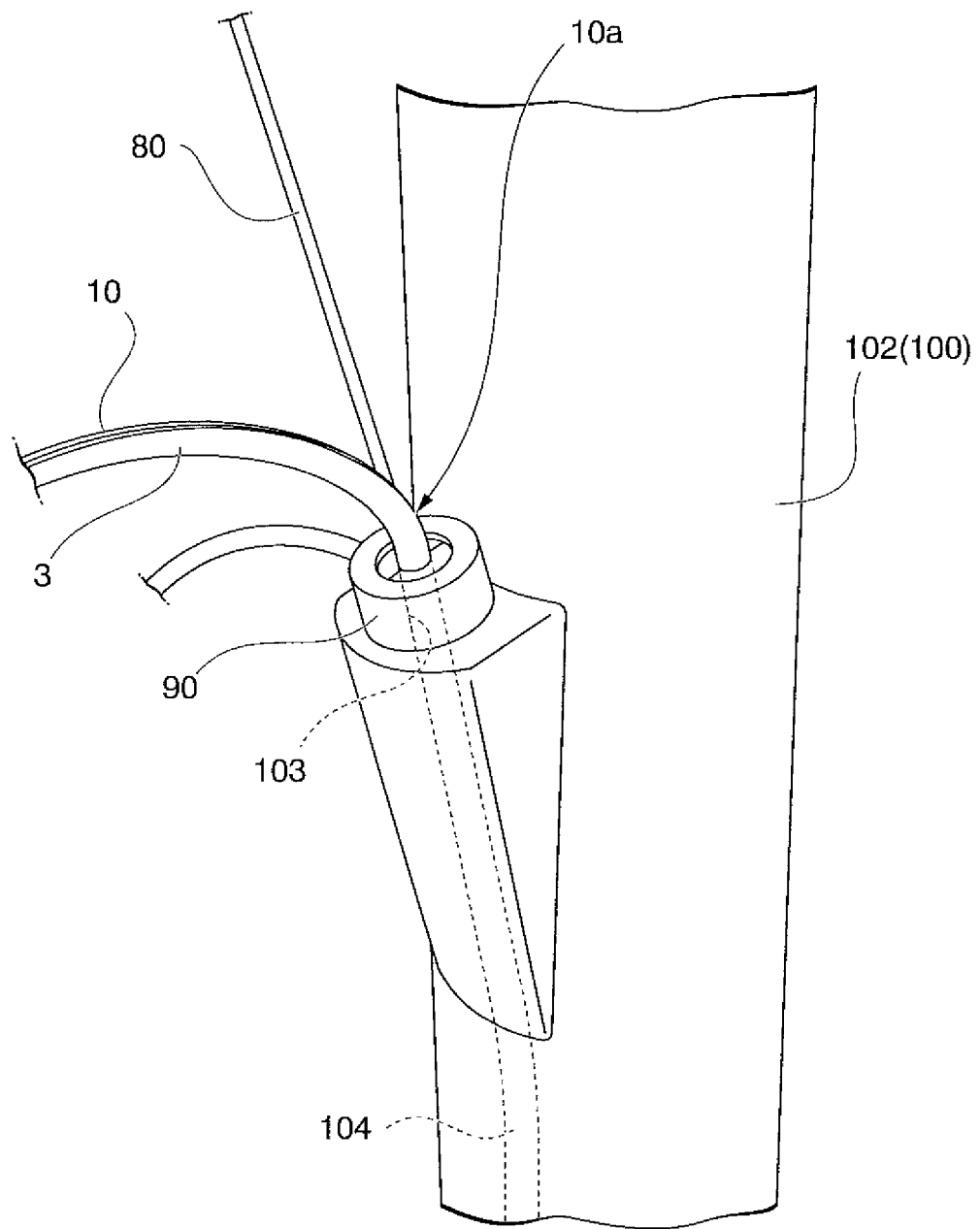
FIG. 19 is a view showing a process in which the sheath and the guide wire of the treatment tool for an endoscope according to the first modification example of the first embodiment are separated from each other.
Figure 20:
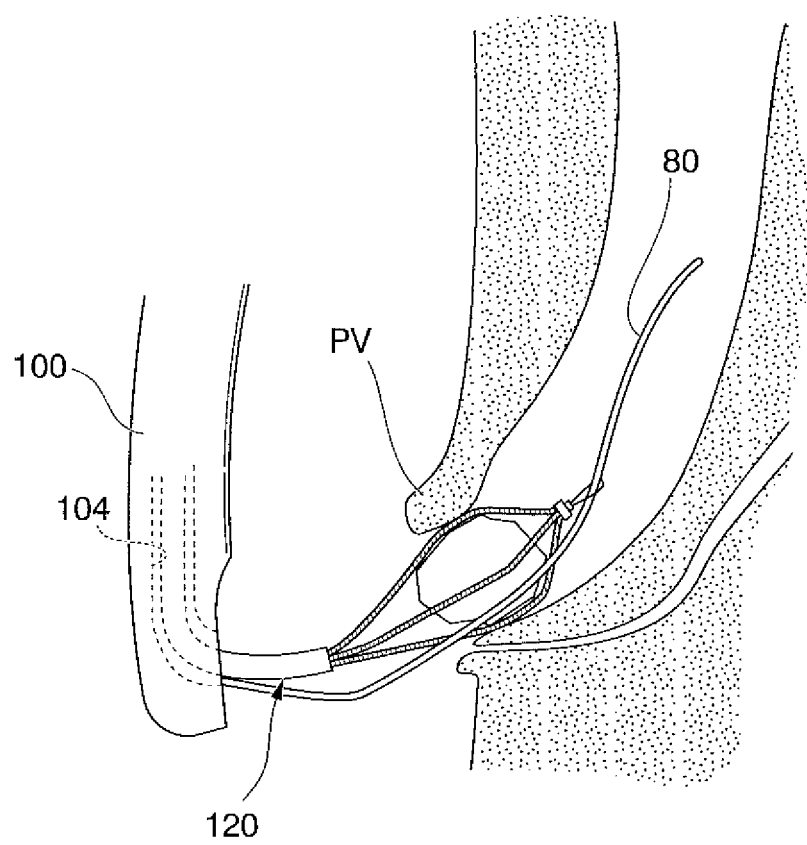
FIG. 20 is a view showing an example of treatment which is performed after the removal of the treatment tool for an endoscope according to the first modification example of the first embodiment.

FIG. 18 is a view showing a process in which the treatment tool 1 for an endoscope is removed from the endoscope apparatus 100 in a state where the guide wire 80 which is attached to the treatment tool 1 for an endoscope in the present modification example remains. FIG. 19 is a view showing a process in which the sheath 3 and the guide wire 80 of the treatment tool 1 for an endoscope are separated from each other. FIG. 20 is a view showing an example of treatment which is performed after the removal of the treatment tool 1 for an endoscope.

After the guide wire 80 reaches a predetermined position, the treatment tool 1 for an endoscope is removed in the state where the guide wire 80 remains in the body. This is performed in order to introduce the known endoscope calculus removal instrument (basket forceps, balloon, or the like) for removing the calculus into the bile duct instead of the treatment tool 1 for an endoscope according to the present embodiment.

As shown in FIG. 18, in order to remove the treatment tool 1 for an endoscope, first, the operator detaches the guide wire 80 from the first port 49, which is disposed in the distal configuration portion 41 of the operation portion 40, through the notch portion 55. At this time, the operator moves the guide wire 80 with respect to the first port 49 from the proximal end 55b of the notch portion 55 of the first port 49 to the distal end 55a of the notch portion 55 through the inner portion of the notch portion 55 without changing the position of the distal end of the guide wire 80. In the process in which the guide wire 80 passes through the notch portion 55 of the first port 49, the guide wire 80 is gradually extracted from the guide wire accommodation portion 9 to the outside of the sheath 3 through the slit portion 10.

Subsequently, as shown in FIG. 19, the operator moves the sheath 3 in the direction of the proximal end of the treatment tool channel 104 while supporting the guide wire 80 such that the position of the guide wire 80 is not changed. In the process in which the operator moves the sheath 3 in the direction of the proximal end of the treatment tool channel 104, the sheath 3 is gradually detached from the guide wire 80.

When the outlet portion 12 (refer to FIG. 10) of the first lumen 7 in the sheath 3 reaches the position of the treatment tool channel port 103, the operator moves the sheath 3 in the direction of the proximal end of the guide wire 80 while supporting the guide wire 80 against the force which is generated by the guide wire 80 to be moved in the direction of the proximal end. The operator extracts the outlet portion 12 of the sheath 3 from the treatment tool channel port 103 without changing the position of the guide wire 80 in the body. Thereafter, the operator moves the distal portion of the sheath 3, in which the outlet portion 12 of the sheath 3 is disposed, in the direction of the proximal end of the guide wire 80, and detaches the sheath 3 from the guide wire 80.

When the sheath 3 is detached from the guide wire 80, the operator attaches the known endoscope calculus removal instrument (for example, basket forceps 120 shown in FIG. 20) to the guide wire 80, and guides the endoscope calculus removal instrument to the calculus which is the removal target through the treatment tool channel 104 of the endoscope apparatus 100.

According to the present modification example, effects similar to those of the above-described embodiment are exerted. As described above, according to the present modification, it is possible to rapidly remove the treatment tool 1 for an endoscope (sheath 3) from the guide wire 80, and it is possible to insert known different treatment tools into the body along the guide wire 80 again. Accordingly, it is possible to rapidly replace the treatment tool.

(Second Modification Example)

Figure 21:
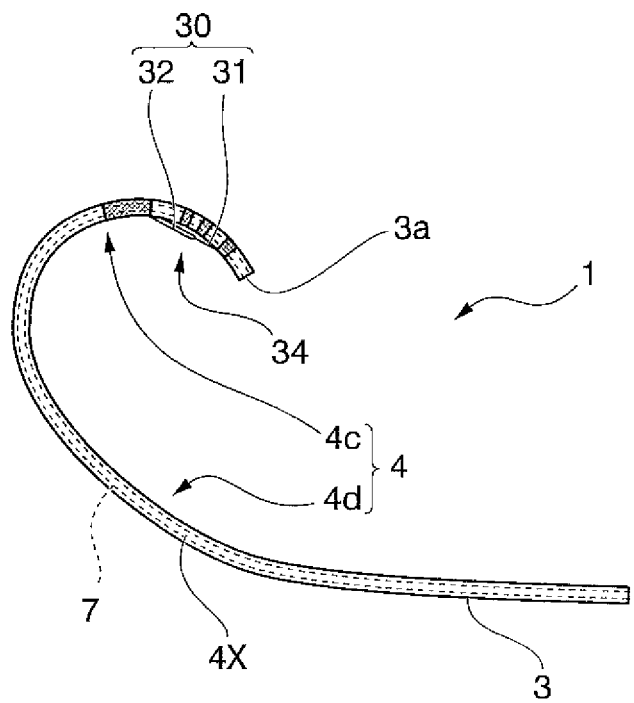
FIG. 21 is a schematic view showing a configuration of a second modification example of the first embodiment of the present invention.

A second modification example of the first embodiment of the present invention will be described. FIG. 21 is a schematic view showing the sheath 3 of the present modification example. As shown in FIG. 21, the pre-curved portion 4 of the present modification example includes a first curved portion 4c (drawing portion) and a second curved portion 4d (copying-deformation portion).

The first curved portion 4c is disposed at the distal end 3a side of the sheath 3, that is, at the distal end 3a side of the pre-curved portion 4. The first curved portion 4c has a predetermined curved shape in a region between the distal end 3a of the sheath 3 and the second distal communication hole 24. The second curved portion 4d is disposed at the proximal side of the pre-curved portion 4. The second curved portion 4d is disposed so as to be adjacent to the first curved portion 4c at the proximal side of the first curved portion 4c, and is curved in the same direction as that of the first curved portion 4c. The outer diameter of the first curved portion is slightly smaller than the outer diameter of the second curved portion 4d. The openings of the first distal communication holes 23 and the second communication holes 24 are disposed at the first curved portion 4c.

When the proximal end of the first curved portion 4c protrudes from the opening portion of the endoscope apparatus 100 toward the outside of the endoscope apparatus 100 (refer to FIG. 13B), the second curved portion 4d is disposed inside the treatment tool channel 104 which is bent by the raising stand 105 or the bendable portion 107 of the endoscope apparatus 100. If the second curved portion 4d is inserted into the treatment tool channel 104 which is bent by the raising stand 105 or the bendable portion 107 of the endoscope apparatus 100, the second curved portion 4d rotates around the center axis of the sheath 3 with respect to the treatment tool channel 104. As a result, in a state where the cutting portion 34 and the pre-curved portion 4 protrude from the opening portion of the endoscope apparatus 100, the bending portion 36 is bent toward the imaging portion 106 side of the endoscope apparatus 100.

The second curved portion 4d functions as a sheath direction guide portion which positions the cutting portion 34 in the direction around the longitudinal axis of the sheath 3. Specifically, the second curved portion 4d guides the direction of the first curved portion 4c such that the curved direction of the first curved portion 4c protruding from the opening portion of the endoscope apparatus 100 to the outside of the endoscope apparatus 100 is directed to the twelve o'clock direction on the endoscopic image captured by the imaging portion 106 of the endoscope apparatus 100.

When the first curved portion 4c is curved in the twelve o'clock direction by the second curved portion 4d is maintained, the cutting portion 34 is directed to a position at which tissues positioned in the direction closer to eleven o'clock relative to the twelve o'clock direction can be incised. Accordingly, in a case where an operator incises the duodenal papilla PV, it is possible to stably perform incision in a state where an amount of bleeding decreases while avoiding blood vessels.

As shown in FIG. 13B, in a state where the distal end portion of the pre-curved portion 4 including the cutting portion 34 enters an imaging visual field of the imaging portion 106, the outer circumferential surface (pressed surface 4X) of the second curved portion 4d is pressed by the raising stand 105.

When the distal portion of the sheath 3 is displayed on the endoscopic image captured by the imaging portion 106 and the curved direction of the pre-curved portion 4 on the endoscopic image is set to twelve o'clock (for example, the state of FIG. 14A), the curved knife portion 35 of the knife wire 30 extends so as to be directed to the position closer to the eleven o'clock direction relative to the twelve o'clock direction due to the shape of the bending portion 36, in addition to the directions of the openings of the first distal communication hole 23 and the second distal communication hole 24. The operator can confirm that the curved knife portion 35 is directed in the direction between eleven o'clock and twelve o'clock on the endoscopic image.

FIG. 14B is a schematic view showing the endoscopic image in a process of treatment using the treatment tool 1 for an endoscope. FIG. 14B shows a state where the distal end portion of the pre-curved portion 4 is disposed in the duodenal papilla PV by a predetermined length. In this state, the slider portion 71 of the operation portion 40 moves from the direction of the proximal end 68b of the shaft portion 68 in the direction of the center axis of the rod-shaped portion 69 of the shaft portion 68, that is, the direction of the center axis L5 (refer to FIG. 2) of the handle-fixing portion 64. Accordingly, the knife wire 30 moves in the direction of the proximal end 30b of the knife wire 30, and the distal end 30a of the knife wire 30 generates force which moves the portion of the first distal communication hole 23 of the sheath 3 in the proximal direction. Therefore, the proximal end portion of the distal end 3a of the sheath 3 is deformed to be curved across the first distal communication hole 23 and the second distal communication hole 24. The cutting portion 34 of the knife wire 30 is suspended in an arch shape with respect to the sheath 3.

The curved knife portion 35 (refer to FIG. 6) is positioned at the second quadrant Q2 in the above-described virtual coordinate system. Accordingly, when the curved direction of the pre-curved portion 4 which is imaged as the endoscopic image by the imaging portion 106 is set to twelve o'clock direction, the curved knife portion 35 comes into contact with the inner surface of the opening portion of the duodenal papilla PV at the position which is biased so as to be closer to the eleven o'clock direction relative to the twelve o'clock direction.

In the process in which the curved knife portion 35 is suspended in an arch shape with respect to the sheath 3, the operator supplies a high-frequency current from a high-frequency power supply device to the knife wire 30 through the connector 73 of the operation portion 40. Accordingly, the tissues which come into contact with the curved knife portion 35 are incised by the high-frequency current. The curved knife portion 35 is curved in a natural state where external force is not applied to the curved knife portion 35. Since the knife wire 30 is moved in the direction of the proximal end 68b of the shaft portion 68 by the slider portion 71, the curved knife portion 35 is gradually deformed from the curved shape in the natural state into a straight-line shape. Specifically, the curved knife portion 35 is gradually deformed from the curved shape in the natural state into the straight-line shape along the straight-line direction in which the first distal communication hole 23 and the second distal communication hole 24 are connected to each other. If the curvature radius of the pre-curved portion 4 is set to be large, the knife wire 30 is gradually deformed from a straight-line shape into a curved shape. In this way, the curved state of the curved knife portion 35 is changed by the movement of the knife wire 30 which uses the slider portion 71.

Since the position of the duodenal papilla PV avoiding a main blood vessel is set so as to be reflected from eleven o'clock on the endoscopic image and the duodenal papilla PV is incised by the curved knife portion 35 at the position of eleven o'clock, it is possible to perform incision in a state where the amount of bleeding due to the incision of the duodenal papilla PV decreases.

Figure 22:
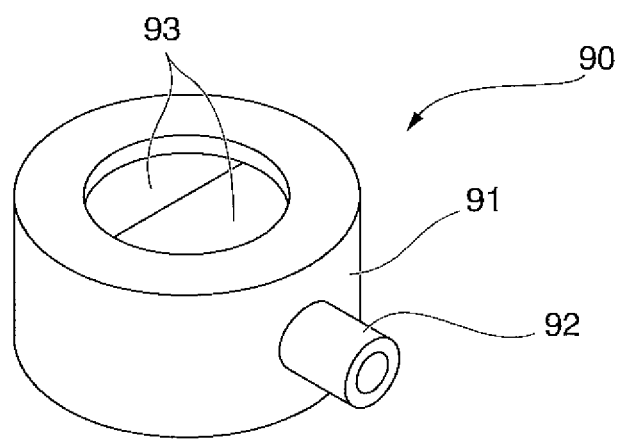
FIG. 22 is a perspective view showing a treatment tool attachment-assisting instrument which can be attached to the endoscope apparatus according to the first embodiment of the present invention.
Figure 23:
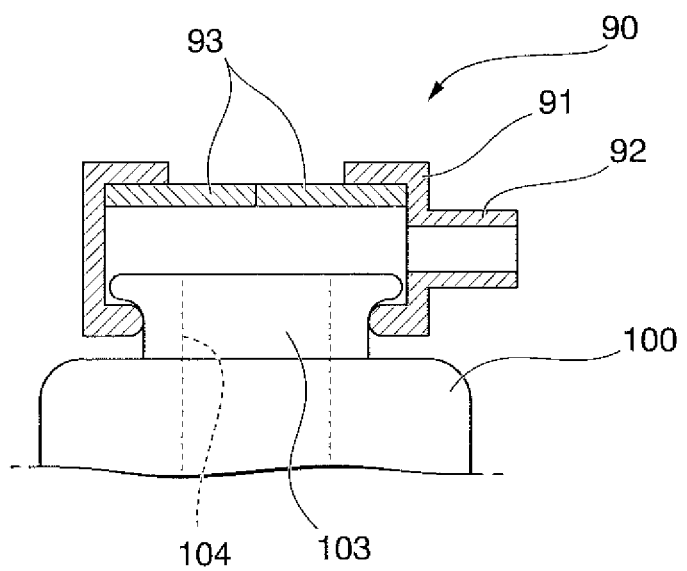
FIG. 23 is a partial sectional view showing an internal structure of the treatment tool attachment-assisting instrument shown in FIG. 22.
Figure 24:
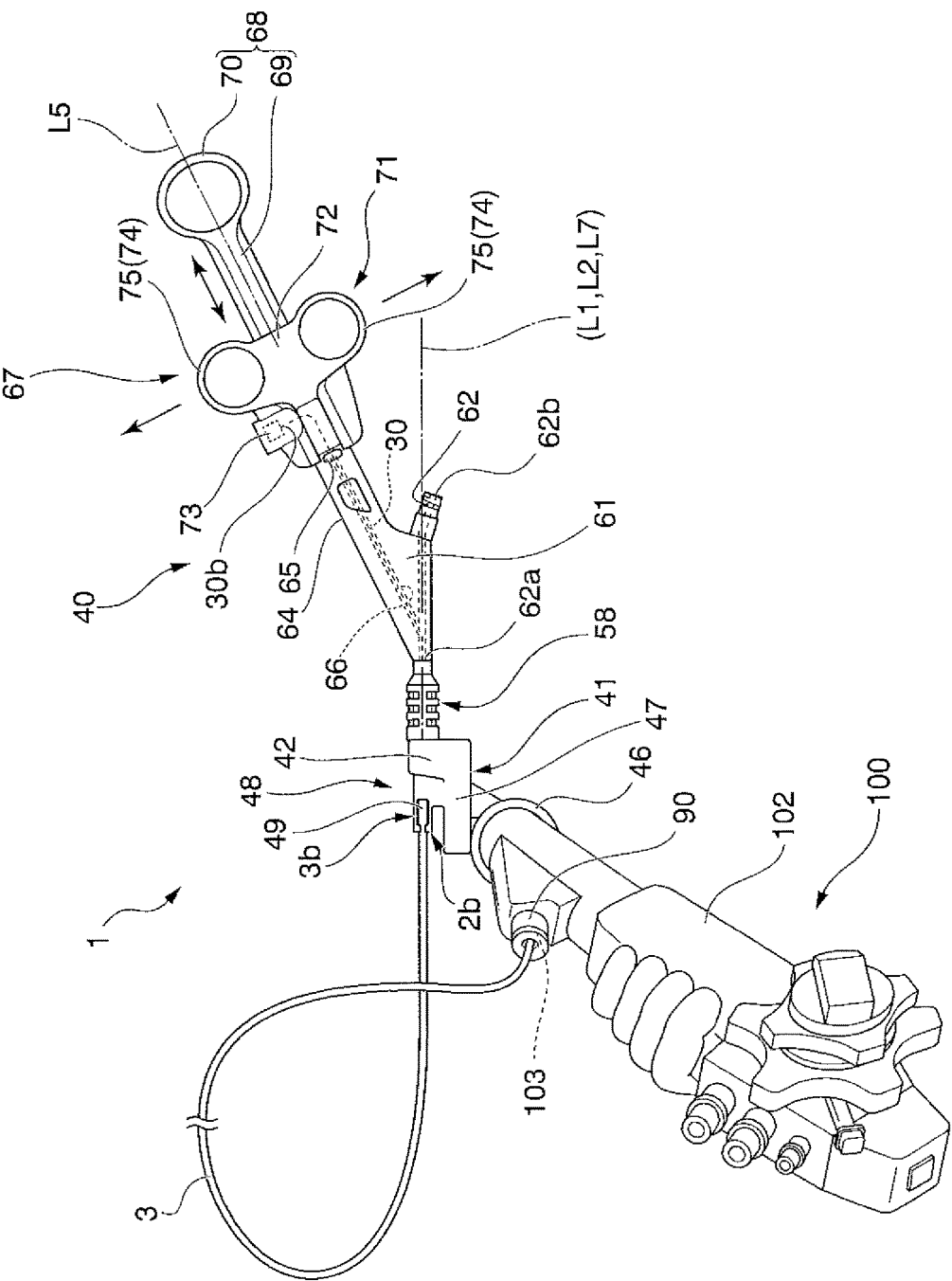
FIG. 24 is a view when the state where the treatment tool for an endoscope according to the first embodiment of the present invention is attached to the endoscope apparatus is viewed from a viewpoint of an operator of the endoscope apparatus.
Figure 25:
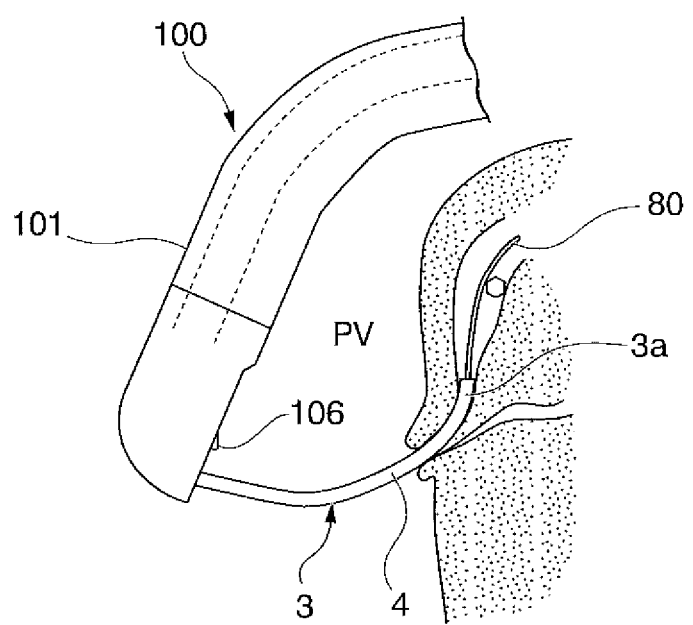
FIG. 25 is a view showing a process when the treatment tool for an endoscope according to the first embodiment of the present invention is used.

Next, a configuration of a treatment tool attachment-assisting instrument 90 will be described, which can be used in the procedure in which the treatment tool for an endoscope according to the present embodiment or the modification examples is attached to the endoscope apparatus 100. FIG. 22 is a perspective view showing the treatment tool attachment-assisting instrument 90 which can be attached to the endoscope apparatus 100. FIG. 23 is a partial sectional view showing an internal structure of the treatment tool attachment-assisting instrument 90.

As shown in FIGS. 22 and 23, the treatment tool attachment-assisting instrument 90 includes an assisting instrument main body 91, a discharge tube 92, and a plug body 93. The assisting instrument main body 91 has a tubular shape which can be fixed to the treatment tool channel port 103 of the endoscope apparatus 100. The discharge tube 92 communicates with the internal space of the assisting instrument main body 91. The plug body 93 is disposed on an extension line extended along the center axis of the treatment tool channel 104 from the proximal opening of the treatment tool channel 104 in the treatment tool channel port 103.

The assisting instrument main body 91 has an attachment structure which can be water-tightly connected to the treatment tool channel port 103. The discharge tube 92 can be connected to a pipeline which is connected to a liquid-discharge container (not shown). The plug body 93 is a soft member which has an opening or a gap through which the plug body 93 can come into close contact with the outer circumferential surface 3c of the sheath 3.

In the present embodiment, the treatment tool attachment-assisting instrument 90 is fixed to the treatment tool channel port 103 of the endoscope apparatus 100 before the treatment tool 1 for an endoscope is inserted into the treatment tool channel 104 (refer to FIG. 19). In the state where the treatment tool attachment-assisting instrument 90 is attached to the treatment tool channel port 103, liquid, which flows in reverse from the distal side of the treatment tool channel 104 of the endoscope apparatus 100 toward the proximal side thereof, mainly flows through the discharge tube 92. Accordingly, the liquid, which flows in reverse from the distal side of the treatment tool channel 104 of the endoscope apparatus 100 toward the proximal side thereof, is very unlikely to leak from the plug body 93 to the outside of the treatment tool attachment-assisting instrument 90.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An electrosurgical incision system, comprising:
   an endoscope that includes:
      an imager capable of taking an image of a target portion,
      an insertion portion that has a treatment tool channel communicating with an opening portion disposed adjacent to the imager, the insertion portion being configured to be inserted into a body during use, and
      a bendable portion that is disposed along a portion of the insertion portion and that is configured to bend the treatment tool channel;
   a sheath that has a center axis extending along a longitudinal axis, the sheath being configured to be inserted into the treatment tool channel;
      the sheath having a pre-curved portion at a distal portion of the sheath, the pre-curved portion being configured to restore to a curved shape in which the center axis of the sheath is curved along a predetermined virtual plane,
      an outer circumferential surface of the sheath having a first communication opening and a second communication opening that communicate with a knife wire lumen within the sheath,
         the first communication opening being positioned on the outer circumferential surface of the sheath at an inward side of the curved shape, and the first communication opening extending along a first longitudinal axis that is inclined to the virtual plane, and
         the second communication opening being positioned proximally of the first communication opening on the outer circumferential surface of the sheath and at the inward side of the curved shape, the second communication opening extending along a second longitudinal axis that is inclined to the virtual plane; and
   a wire that is configured to incise tissue and that is disposed through the first communication opening and the second communication opening, the wire including:
      a distal end portion that is at least partly disposed within the knife wire lumen,
      a curved knife portion that is connected to the distal end portion, the curved knife portion being positioned outside of the sheath, and
      a bent portion that is laterally bent from the first longitudinal axis of the first communication opening, the bent portion being disposed between the distal end portion and the curved knife portion such that the bent portion is disposed radially outward of the outer circumferential surface of the sheath,
   wherein, when the pre-curved portion forms the curved shape, a plane that intersects the first communication opening and the second communication opening is laterally offset from the curved knife portion and is laterally offset from the center axis of the sheath, and
   wherein, when the sheath is positioned inside of the treatment tool channel, the pre-curved portion of the sheath is configured to rotate around the longitudinal axis of the sheath so that a bent shape of the pre-curved portion coincides with a bent shape of the treatment tool channel.

2. The electrosurgical incision system according to claim 1, wherein:
   a distal end portion of the pre-curved portion is a first curved portion that has a first restoring force so as to be restored to the curved shape in which the center axis of the sheath is included in the virtual plane,
   a proximal end portion of the pre-curved portion is a second curved portion that is continuous with a proximal end of the first curved portion, the second curved portion having a second restoring force so as to be restored to the curved shape in the same direction as that of the first curved portion, and the second curved portion determining a position of the curved knife portion in the direction around the longitudinal axis of the sheath,
   wherein:
      when the second curved portion is inserted through the treatment tool channel of the endoscope and the treatment tool channel is bent, the second curved portion is configured to be rotated around the center axis of the sheath with respect to the treatment tool channel, and the distal end portion of the pre-curved portion is directed in a predetermined direction when the second curved portion protrudes from the opening portion of the endoscope, and
      a bending portion of the treatment tool channel is bent toward the imager of the endoscope in a state that the distal end portion of the pre-curved portion protrudes from the opening portion of the endoscope.

3. The electrosurgical incision system according to claim 1, further including a guide wire accommodation portion that is parallel with the knife wire lumen in the sheath, and
   wherein a slit is formed in the sheath such that the slit is parallel with the center axis of the sheath, the slit being formed in an outer surface of the pre-curved portion at a position at which the pre-curved portion intersects with the virtual plane to communicate with the guide wire accommodation portion.

4. The electrosurgical incision system according to claim 1, wherein in a state when the curved knife portion and a distal end of the pre-curved portion are within an imaging visual field of the imager, the outer circumferential surface of the sheath is pressed by a raising stand.

* * * * *